United States Patent
Dai et al.

(10) Patent No.: US 8,778,219 B2
(45) Date of Patent: Jul. 15, 2014

(54) IONIC LIQUIDS FOR SEPARATION OF OLEFIN-PARAFFIN MIXTURES

(71) Applicant: UT-Battelle, LLC, Oak Ridge, TN (US)

(72) Inventors: Sheng Dai, Knoxville, TN (US);
Huimin Luo, Knoxville, TN (US);
Jing-Fang Huang, Pingtung (TW)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 13/969,717

(22) Filed: Aug. 19, 2013

(65) Prior Publication Data
US 2013/0338389 A1    Dec. 19, 2013

Related U.S. Application Data

(62) Division of application No. 12/502,695, filed on Jul. 14, 2009, now Pat. No. 8,535,560.

(51) Int. Cl.
*C07F 1/10* (2006.01)
*C09K 3/00* (2006.01)

(52) U.S. Cl.
USPC .......................................... 252/184; 556/111

(58) Field of Classification Search
USPC ................................. 252/184; 556/111, 114
See application file for complete search history.

(56) References Cited

U.S. PATENT DOCUMENTS

| 7,423,164 B2 | 9/2008 | Dai et al. |
| 2005/0154247 A1 | 7/2005 | Jong et al. |
| 2008/0070817 A1 | 3/2008 | Qu et al. |

OTHER PUBLICATIONS

Aliaga C. et al., "Surface Chemistry of Room-Temperature Ionic Liquids", Physical Chemistry Chemical Physics 9:3683-3700 (2007).
Burns R.L. et al., "Defining the Challenges for C3H6/C3H8 Separation Using Polymeric Membranes", Journal of Membrane Science 211:299-309 (2003).
DesMarteau D.D., "Novel Perfluorinated Ionomers and Ionenes";, Journal of Fluorine Chemistry 72:203-208 (1995).
Donnio B. et al., "Liquid-Crystalline, Polycatenar Complexes of Silver(I): Dependence of the Mesomorphism on the Ligand and the Anion", New J. Chem. 275-286 (1999).
Gorri D. et al., "The Use of Ionic Liquids as Efficient Extraction Medium in the Reactive Separation of Cycloolefins from Cyclohexane", Chemical Engineering Journal 154:241-245 (2009).
Huang J-F et al., "Advanced Liquid Membranes Based on Novel Ionic Liquids for Selective Separation of Olefin/Paraffin Via Olefin-Facilitated Transport", Industrial & Engineering Chemistry Research 47(3):881-888 (2008).
Nockemann P. et al., "Polynuclear Metal Complexes Obtained from the Task-Specific Ionic Liquid Betainium Bistriflimide", Crystal Growth & Design 8(4):1353-1363 (2008).
Qu J. et al., "Ionic Liquids as Novel Lubricants and Additives", Oak Ridge National Laboratory pp. 1-23.
Seddon K.R., "Ionic Liquids—A Taste of the Future", Nature Materials 2:363-365 (2003).
Xue L. et al., "Perfectly Staggered and Twisted Difluoromethylene Groups in Perfluoroalkyl Chains: Structure of M [C4F9SO2NSO2C4F9] (M=Na,K)" Angew. Chem. Int. Ed. Engl. 36(12):-1331-1332 (1997).
International Search Report and Written Opinion dated Feb. 21, 2011 received from the Korean Intellectual Property Office issued in corresponding International Application No. PCT/US2010/041647.

*Primary Examiner* — Peter F Godenschwager
(74) *Attorney, Agent, or Firm* — Scully, Scott, Murphy & Presser, P.C.

(57) ABSTRACT

The invention is directed to an ionic liquid comprising (i) a cationic portion containing a complex of a silver (I) ion and one or more neutral ligands selected from organoamides, organoamines, olefins, and organonitriles, and (ii) an anionic portion having the chemical formula

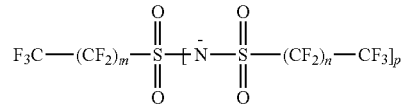

wherein m and n are independently 0 or an integer of 1 or above, and p is 0 or 1, provided that when p is 0, the group —N—SO$_2$—(CF$_2$)$_n$CF$_3$ subtended by p is replaced with an oxide atom connected to the shown sulfur atom. The invention is also directed to a method for separating an olefin from an olefin-paraffin mixture by passing the mixture through a layer of the ionic liquid described above.

19 Claims, No Drawings

IONIC LIQUIDS FOR SEPARATION OF OLEFIN-PARAFFIN MIXTURES

CROSS REFERENCE TO RELATED APPLICATIONS

This application is a divisional of U.S. application Ser. No. 12/502,695 filed on Jul. 14, 2009, the contents of which are incorporated herein by reference in their entirety.

This invention was made with government support under Contract Number DE-AC05-00OR22725 between the United States Department of Energy and UT-Battelle, LLC. The U.S. government has certain rights in this invention.

FIELD OF THE INVENTION

The present invention relates generally to the field of ionic liquids, and more particularly, to silver-containing ionic liquids.

BACKGROUND OF THE INVENTION

One of the process steps employed in petroleum refining is the separation of olefins from paraffin-rich streams. Low-temperature distillation is commonly used for this purpose. See, for example, Bryan, P. F., "Removal of propylene from fuel-grade propane. *Separation and Purification Reviews*, 33, 157-182 (2004). However, distillation processes tend to be both capital and energy intensive due in large part to the low relative volatilities of the olefin and paraffin components.

Facilitated-transport membranes (e.g., immobilized liquid membranes, or ILMs) have also been used for the separation of olefins and paraffins. When used for this purpose, the ILM typically contains an olefin-transporting metal ion (e.g., $Ag^+$) dissolved in a solvent. Such ILMs are generally selective toward olefins and have fast diffusion rates. However, they are known to suffer from a significant degree of instability due to solvent vaporization and air oxidation. Solid polymer membranes are also known for this purpose. They generally possess improved stabilities. However, a significant drawback of solid polymer membranes is their slow diffusion.

Accordingly, there is a need for liquid olefin-paraffin separation compositions which have an improved stability while possessing at least the diffusion rates and selectivities of liquid olefin-paraffin membrane compositions of the art. There is also a particular need for olefin-paraffin separation compositions having a higher silver ion content than found in conventional liquid-supported and polymer-supported membranes. The higher silver ion content would advantageously serve to increase the transport flux of olefins.

SUMMARY OF THE INVENTION

In one aspect, the invention is directed to an ionic liquid comprising (i) a cationic portion containing a complex of a silver (I) ion and one or more neutral ligands selected from organoamides, organoamines, olefins, and organonitriles, and (ii) an anionic portion having the chemical formula

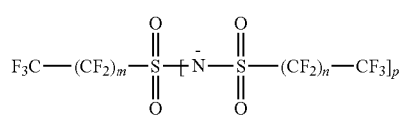

(5)

wherein m and n are independently 0 or an integer of 1 or above, and p is 0 or 1, provided that when p is 0, the group $-N-SO_2-(CF_2)_nCF_3$ subtended by p is replaced with an oxide atom connected to the shown sulfur atom, and when p is 1, the shown perfluoroalkyl groups can optionally crosslink to form a cyclic anion.

The ionic liquid (IL) compositions of the invention are useful for separating an olefin from a paraffin in an olefin-paraffin gas mixture. Accordingly, in another aspect, the invention is directed to an olefin-paraffin separation membrane which contains a layer of the ionic liquid, as described above, on or in an inert gas-permeable support. In yet another aspect, the invention is directed to a method for separating an olefin from a paraffin contained in a gaseous olefin-paraffin mixture, the method involving passing the gaseous olefin-paraffin mixture through a layer of ionic liquid described above.

In a preferred embodiment, the ionic liquids have an improved stability while possessing at least the diffusion rates and selectivities of liquid membrane compositions of the art. In other preferred embodiments, the ionic liquids of the invention possess improved diffusion rates and selectivities than liquid membrane compositions of the art while possessing an improved stability. The ionic liquids of the invention also advantageously possess a higher silver ion content than found in conventional liquid-supported and polymer-supported olefin-paraffin separation membranes.

The ionic liquids of the invention provide the above improvements by judicious selection of the anion and cation portions of the ionic liquid. In regard to the anion, advantageous properties can be imparted to the ionic liquids of the invention by use of an anionic portion which is larger in size (i.e., in molecular weight or volume) than the anions traditionally used in the art. Some examples of anions traditionally used in the art of ionic liquids include bis(trifluoromethylsulfonyl)imide (i.e., $(CF_3SO_2)_2N^-$ or $Tf_2N$), $BF_4^-$, $NO_3^-$, $SO_4^{2-}$, $PO_4^{3-}$, $PF_6^-$ and dicyanamide (i.e., $N(CN)_2^-$), as described, for example, in U.S. Pat. No. 7,423,164. Other advantageous properties can be imparted to the ionic liquids of the invention by use of an asymmetrical anion. Formula (5) above encompasses numerous anions which possess either an increased size (i.e., when m+n is at least 1) or an asymmetry (i.e., when p is 1, and m and n are different; or when p is 0). Several of the advantageous or improved properties of the inventive ionic liquids make them improved olefin-paraffin separation compositions. Some of the improved properties may include, for example, an increased stability, greater permeability (e.g., by a decreased viscosity), increased hydrophobicity, and/or an increased selectivity in olefin transport.

DETAILED DESCRIPTION OF THE INVENTION

The terms "hydrocarbon group" and "hydrocarbon linker", as used herein, are, in a first embodiment, composed solely of carbon and hydrogen. In different embodiments, one or more of the hydrocarbon groups or linkers can contain precisely, or a minimum of, or a maximum of, for example, one, two, three, four, five, six, seven, eight, nine, ten, eleven, twelve, thirteen, fourteen, fifteen, sixteen, seventeen, or eighteen carbon atoms, or a particular range of carbon atoms between any of the foregoing carbon numbers. Hydrocarbon groups of different ionic liquid compounds described herein may possess the same or different number (or preferred range thereof) of carbon atoms in order to suitably optimize one or more characteristics of each ionic liquid compound.

The hydrocarbon groups or linkers can be, for example, saturated and straight-chained (i.e., straight-chained alkyl groups or alkylene linkers). Some examples of straight-chained alkyl groups (or alkylene linkers) include methyl (or methylene, $-CH_2-$), ethyl (or ethylene or dimethylene, i.e., —CH$_2$CH$_2$—), n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, and n-octadecyl groups.

The hydrocarbon groups or linkers can alternatively be saturated and branched (i.e., branched alkyl groups or alkylene linkers). Some examples of branched alkyl groups include isopropyl, isobutyl, sec-butyl, t-butyl, isopentyl, neopentyl, 2-methylpentyl, 3-methylpentyl, and the numerous C$_7$, C$_8$, C$_9$, C$_{10}$, C$_{11}$, C$_{12}$, C$_{13}$, C$_{14}$, C$_{15}$, C$_{16}$, C$_{17}$, and C$_{18}$ saturated and branched hydrocarbon groups. Some examples of branched alkylene linkers are those derived by removal of a hydrogen atom from one of the foregoing exemplary branched alkyl groups.

The hydrocarbon groups or linkers can alternatively be saturated and cyclic (i.e., cycloalkyl groups or cycloalkylene linkers). Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane). Some examples of cycloalkylene linkers are those derived by removal of a hydrogen atom from one of the foregoing exemplary cycloalkyl groups.

The hydrocarbon groups or linkers can alternatively be unsaturated and straight-chained (i.e., straight-chained olefinic or alkenyl groups or linkers). Some examples of straight-chained olefinic groups include vinyl, 2-propen-1-yl, 3-buten-1-yl, 2-buten-1-yl, butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), and the numerous C$_7$, C$_8$, C$_9$, C$_{10}$, C$_{11}$, C$_{12}$, C$_{13}$, C$_{14}$, C$_{15}$, C$_{16}$, C$_{17}$, and C$_{18}$ unsaturated and straight-chained hydrocarbon groups. Some examples of straight-chained olefinic linkers are those derived by removal of a hydrogen atom from one of the foregoing exemplary straight-chained olefinic groups.

The hydrocarbon groups or linkers can alternatively be unsaturated and branched (i.e., branched olefinic or alkenyl groups or linkers). Some examples of branched olefinic groups include 2-propen-2-yl, 3-buten-2-yl, 3-buten-3-yl, 4-penten-2-yl, 4-penten-3-yl, 3-penten-2-yl, 3-penten-3-yl, 2,4-pentadien-3-yl, and the numerous C$_6$, C$_7$, C$_8$, C$_9$, C$_{10}$, C$_{11}$, C$_{12}$, C$_{13}$, C$_{14}$, C$_{15}$, C$_{16}$, C$_{17}$, and C$_{18}$ unsaturated and branched hydrocarbon groups. Some examples of branched olefinic linkers are those derived by removal of a hydrogen atom from one of the foregoing exemplary branched olefinic groups.

The hydrocarbon groups or linkers can alternatively be unsaturated and cyclic (i.e., cycloalkenyl groups or cycloalkenylene linkers). Some examples of unsaturated and cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group can also be a polycyclic (e.g., bicyclic) group by either possessing a bond between two of the ring groups (e.g., biphenyl) or a shared (i.e., fused) side (e.g., naphthalene, anthracene, and phenanthrene). Some examples of cycloalkenylene linkers are those derived by removal of a hydrogen atom from one of the foregoing exemplary cycloalkenyl groups.

One or more of the hydrocarbon groups may also include one or more heteroatoms, such as one or more oxygen, nitrogen, sulfur, or halide atoms. Some examples of oxygen-containing groups include hydroxyl (OH) groups, carbonyl groups (e.g., ketone, aldehyde, ester, amide, or urea functionalities), and carbon-oxygen-carbon (ether) groups. The ether group can also be a polyalkyleneoxide group, such as a polyethyleneoxide group. Some examples of nitrogen-containing groups include primary amine groups, secondary amine groups, tertiary amine groups, quaternary amine groups, cyanide group, amide group (i.e., —C(O)NR$_2$, wherein R is selected from hydrogen atom and hydrocarbon group), nitro group, urea group, and carbamate group, wherein it is understood that a quaternary amine group necessarily possesses a positive charge and requires a counteranion. Some examples of sulfur-containing groups include the thioether (i.e., sulfide), disulfide, sulfoxide, sulfone, sulfonate, and sulfate groups. Halide atoms considered herein include fluorine, chlorine, and bromine. Some examples of fluorine-containing hydrocarbon groups (i.e., fluorocarbon groups) include the partially-substituted varieties (e.g., fluoromethyl, difluoromethyl, 2-fluoroethyl, 2,2-difluoroethyl, 2,2,2-trifluoroethyl, and the like) and perfluoro-substituted varieties (e.g., perfluoromethyl, perfluoroethyl, perfluoropropyl, perfluorobutyl, and the like).

In one aspect, the invention is directed to novel ionic liquid compositions. The ionic liquids of the invention include (i) a cationic portion containing a complex of a silver (I) ion (i.e., Ag$^+$) and one or more neutral ligands, and (ii) an anionic portion. Typically, the Ag$^+$-ligand complex possesses the general formula AgY$^+$ or AgY$_2^+$, wherein Y herein denotes a neutral ligand. However, other formulas are contemplated herein for the cation portion, including, for example, AgY$_3^+$, Ag$_2$Y$^{2+}$, Ag$_2$Y$_2^{2+}$, Ag$_2$Y$_3^{2+}$, Ag$_3$Y$_2^{3+}$, and Ag$_3$Y$_3^{3+}$. In addition, where more than one Y is present, the Y neutral ligands may be the same or different.

In one embodiment, the one or more neutral ligands complexed to silver (I) are selected from the class of organoamide compounds. The organoamide compounds considered herein are those compounds containing the carboxamide (i.e., —C(O)N—) functionality (also known as organocarboxamide compounds). In a particular embodiment, the organoamides have a chemical formula within the following generic formula:

(1)

In formula (1) above, R$_1$, R$_2$, and R$_3$ are independently selected from a hydrogen atom and any of the hydrocarbon groups described above. In a particular embodiment, R$_1$ and R$_2$ are independently selected from a hydrogen atom or a hydrocarbon group containing at least one, two, or three, and up to four, five, or six carbon atoms, and R$_3$ is selected from a hydrogen atom or a hydrocarbon group containing at least one, two, or three, and up to four, five, six, seven, eight, nine, ten, eleven, or twelve carbon atoms. Preferably, if one or more heteroatoms are present in R$_1$, R$_2$, and/or R$_3$, the heteroatoms are not directly attached to the shown carboxamide nitrogen atom or carbonyl group.

In one embodiment of formula (1), R$_3$ does not contain a phenyl ring directly attached to the carboxamide group shown in formula (1). In a first embodiment thereof, R$_1$, R$_2$, and R$_3$ are all hydrogen atoms, which corresponds to the compound formamide.

In a second embodiment of formula (1), $R_1$ and $R_2$ are hydrogen atoms, while $R_3$ is a hydrocarbon group. Some examples of such organoamide compounds include acetamide (i.e., ethanamide), propionamide, butyramide, isobutyramide, pentanamide (i.e., valeramide), isopentanamide, hexanamide, heptanamide, octanamide, 2-hydroxyacetamide (i.e., glycolamide), 2-hydroxypropionamide, 3-hydroxypropionamide, 4-hydroxybutanamide, 2-methoxyacetamide, 3-ethoxypropionamide, 2-aminoacetamide (i.e., glycinamide), 3-aminopropionamide, 4-aminobutanamide (i.e., 4-aminobutyramide), 2-fluoroacetamide, 3-fluoropropionamide, cyclohexanecarboxamide, 2-cyclohexylacetamide, acrylamide, methacrylamide, 2-phenylacetamide, 3-phenylpropionamide, 2-amino-3-phenylpropionamide, 4-phenylbutanamide, 3-butynamide, 2-hydroxy-4-phenylbutanamide, trifluoroacetamide, pentafluoropropionamide, malonamide, succinamide, glutaramide, adipamide, fumaramide, and acetylenedicarboxamide.

In a third embodiment of formula (1), one of $R_1$ and $R_2$ is a hydrocarbon group, while $R_3$ is a hydrogen atom. Some examples of such organoamide compounds include N-methylformamide, N-ethylformamide, N-n-propylformamide, N-isopropylformamide, N-n-butylformamide, N-isobutylformamide, N-sec-butylformamide, N-t-butylformamide, N-n-pentylformamide, N-isopentylformamide, N-neopentylformamide (i.e., 3,3-dimethylbutanamide), 2-methylpentanamide, N-n-hexylformamide, N-n-heptylformamide, N-n-octylformamide, N-cyclohexylformamide, N-phenylformamide, N-benzylformamide, N-vinylformamide, N-allylformamide, N-(2-propynyl)formamide, N-(hydroxymethyl)formamide, N-(2-hydroxyethyl)formamide, N-(2-hydroxypropyl)formamide, N-(3-hydroxypropyl)formamide, N-(2-hydroxybutyl)formamide, N-(4-hydroxybutyl)formamide, N-(2-methoxyethyl)formamide, N-(aminomethyl)formamide, and N-(2-aminoethyl)formamide.

In a fourth embodiment of formula (1), both of $R_1$ and $R_2$ are hydrocarbon groups, while $R_3$ is a hydrogen atom. Some examples of such organoamide compounds include N,N-dimethylformamide, N-methyl-N-ethylformamide, N,N-diethylformamide, N-methyl-N-n-propylformamide, N-methyl-N-n-propylformamide, N-methyl-N-isopropylformamide, N-methyl-N-n-butylformamide, N-ethyl-N-n-butylformamide, N-methyl-N-isobutylformamide, N-methyl-N-t-butylformamide, N-methyl-N-n-pentylformamide, N-methyl-N-isopentylformamide, N-methyl-2-methylpentanamide, N-methyl-N-n-hexylformamide, N-methyl-N-n-heptylformamide, N-methyl-N-n-octylformamide, N,N-di-n-propylformamide (i.e., N,N-dipropylformamide), N,N-diisopropylformamide, N,N-di-n-butylformamide (i.e., N,N-dibutylformamide or DBF), N,N-diisobutylformamide, N-methyl-N-vinylformamide, N-methyl-N-allylformamide, N-methyl-N-(2-propynyl)formamide, N-methyl-N-(hydroxymethyl)formamide, N-methyl-N-(2-hydroxyethyl)formamide, N-methyl-N-(2-hydroxypropyl)formamide, N-methyl-N-(3-hydroxypropyl)formamide, N-methyl-N-(4-hydroxybutyl)formamide, N-methyl-N-(2-methoxyethyl)formamide, N-methyl-N-(aminomethyl)formamide, and N-methyl-N-(2-aminoethyl)formamide.

In a fifth embodiment of formula (1), one of $R_1$ and $R_2$ is a hydrocarbon group, while $R_3$ is a hydrocarbon group. Some examples of such organoamide compounds include the N-methyl-, N-ethyl-, N-n-propyl-, N-isopropyl-, N-n-butyl-, N-isobutyl-, N-sec-butyl-, N-t-butyl-, N-n-pentyl-, N-isopentyl-, N-neopentyl-, N-vinyl-, N-allyl-, N-phenyl-, N-benzyl-, N-(2-propynyl)-, N-cyclopentyl-, N-cyclohexyl-, N-hydroxymethyl-, N-(2-hydroxyethyl)-, N-(2-hydroxypropyl), N-(2-hydroxybutyl), N-(2-methoxyethyl), N-(aminomethyl), and N-(2-aminoethyl) derivatives of: acetamide (i.e., ethanamide), propionamide, butyramide, isobutyramide, pentanamide (i.e., valeramide), isopentanamide, hexanamide, heptanamide, octanamide, nonanamide, decanamide, dodecanamide, 2-hydroxyacetamide (i.e., glycolamide), 2-hydroxypropionamide, 3-hydroxypropionamide, 4-hydroxybutanamide, 2-methoxyacetamide, 3-ethoxypropionamide, 2-aminoacetamide (i.e., glycinamide), 2-aminopropionamide, 3-aminopropionamide, 4-aminobutanamide (i.e., 4-aminobutyramide), 2-fluoroacetamide, 3-fluoropropionamide, cyclohexanecarboxamide, 2-cyclohexylacetamide, acrylamide, methacrylamide, 2-phenylacetamide, 3-phenylpropionamide, 2-amino-3-phenylpropionamide, 4-phenylbutanamide, 3-butynamide, 2-hydroxy-4-phenylbutanamide, and trifluoroacetamide.

In a sixth embodiment of formula (1), $R_1$, $R_2$, and $R_3$ are all hydrocarbon groups. Some examples of such organoamide compounds include the N,N-dimethyl-, N,N-diethyl-, N,N-di-n-propyl-, N,N-diisopropyl-, N,N-di-n-butyl-, N,N-diisobutyl-, N,N-diallyl-, N,N-bis(2-hydroxyethyl)-, N-methyl-N-ethyl-, N-methyl-N-n-propyl-, N-methyl-N-isopropyl-, N-methyl-N-n-butyl-, N-methyl-N-isobutyl-, N-methyl-N-t-butyl-, N-methyl-N-benzyl-, N-ethyl-N-n-propyl-, N-ethyl-N-isopropyl-, N-ethyl-N-n-butyl-, N-ethyl-N-isobutyl-, N-ethyl-N-t-butyl-, N-ethyl-N-benzyl-, N-n-propyl-N-isopropyl-, N-n-propyl-N-n-butyl-, N-n-propyl-N-isobutyl-, N-n-propyl-N-t-butyl-, N-n-propyl-N-benzyl-, N-isopropyl-N-n-butyl-, N-isopropyl-N-isobutyl-, N-isopropyl-N-t-butyl-, N-isopropyl-N-benzyl-, N-n-butyl-N-isobutyl-, N-n-butyl-N-t-butyl-, N-n-butyl-N-benzyl-, N-isobutyl-N-t-butyl-, N-isobutyl-N-benzyl-, N-methyl-N-n-pentyl-, N-methyl-N-isopentyl-, N-ethyl-N-n-pentyl-, N-ethyl-N-isopentyl-, N-n-propyl-N-n-pentyl-, N-n-propyl-N-isopentyl-, N-isopropyl-N-n-pentyl-, N-isopropyl-N-isopentyl-, N-methyl-N-vinyl-, N-ethyl-N-vinyl-, N-methyl-N-allyl-, N-ethyl-N-allyl-N-methyl-N-(2-propynyl)-, N-methyl-N-(hydroxymethyl)-, N-methyl-N-(2-hydroxyethyl)-, N-ethyl-N-(2-hydroxyethyl)-, N-isopropyl-N-(2-hydroxyethyl)-, N-n-butyl-N-(2-hydroxyethyl)-, N-isobutyl-N-(2-hydroxyethyl)-, N-methyl-N-(2-hydroxypropyl), N-methyl-N-(2-hydroxybutyl), N-methyl-N-(2-methoxyethyl), N-methyl-N-(aminomethyl), and N-methyl-N-(2-aminoethyl) derivatives of: acetamide (i.e., ethanamide), propionamide, butyramide, isobutyramide, pentanamide (i.e., valeramide), isopentanamide, hexanamide, heptanamide, octanamide, nonanamide, decanamide, dodecanamide, 2-hydroxyacetamide (i.e., glycolamide), 2-hydroxypropionamide, 3-hydroxypropionamide, 4-hydroxybutanamide, 2-methoxyacetamide, 3-ethoxypropionamide, 2-aminoacetamide (i.e., glycinamide), 2-aminopropionamide, 3-aminopropionamide, 4-aminobutanamide (i.e., 4-aminobutyramide), 2-fluoroacetamide, 3-fluoropropionamide, cyclohexanecarboxamide, 2-cyclohexylacetamide, acrylamide, methacrylamide, 2-phenylacetamide, 3-phenylpropionamide, 2-amino-3-phenylpropionamide, 4-phenylbutanamide, 3-butynamide, 2-hydroxy-4-phenylbutanamide, and trifluoroacetamide.

In another embodiment of formula (1), one of $R_1$ or $R_2$ can crosslink with $R_3$ to form a cyclic amide (lactam) compound (i.e., one of $R_1$ or $R_2$ can combine with $R_3$ to form a cyclic amide structure). The lactam can be, for example, a $\beta$-, $\gamma$-, $\delta$-, or $\epsilon$-lactam. Some examples of lactam compounds include 2-pyrrolidone, N-methylpyrrolidone, N-vinylpyrrolidone, $\gamma$-valerolactam, $\delta$-valerolactam, and the $\beta$-, $\gamma$-, $\delta$-, and $\epsilon$-caprolactams. In another embodiment, the organoamides of the invention do not include lactam compounds, or more specifically, formula (1) includes the proviso that $R_1$ and $R_2$ cannot crosslink with $R_3$ to form a lactam.

In another embodiment of formula (1), $R_3$ contains a phenyl ring directly attached to the carboxamide group shown in formula (1). These organoamide compounds have a chemical formula within the following generic formula:

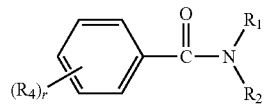

(2)

In formula (2) above, $R_1$ and $R_2$ are independently selected from a hydrogen atom or a hydrocarbon group containing at least one, two, or three, and up to four, five, or six carbon atoms, while $R_4$ is a hydrocarbon group containing at least one, two, or three, and up to four, five, or six carbon atoms. As understood by formula (2), $R_4$ is a hydrocarbon substituent on any one of the available carbon atoms of the shown phenyl ring, wherein a hydrocarbon substituent, when present, is understood to be in place of a hydrogen atom of the phenyl ring. The $R_4$ group can alternatively be any of the heteroatom groups (for example, hydroxy, carboxy, alkoxy, and amine groups) described above. The subscript r can be a value of 0 to 5 to indicate, respectively, 0 to 5 $R_4$ groups present on up to five of the available carbon atoms of the phenyl ring shown in formula (2). In a particular embodiment, the sum of carbon atoms contained by the one or more $R_4$ groups on the shown phenyl ring is six. For example, in this embodiment, if one $R_4$ group is present and is a hydrocarbon group, it contains no more than six carbon atoms, whereas if two $R_4$ groups are present and are both hydrocarbons, the two $R_4$ groups contain either 1 and 5, or 2 and 4, or 3 and 3 carbon atoms, respectively, such that the sum of carbon atoms is 6.

In one embodiment of formula (2), r is 0 (and thus, no $R_4$ substituents on the shown phenyl ring), and $R_1$ and $R_2$ are hydrogen atoms. In this case, the organoamide compound shown by formula (2) is benzamide.

In another embodiment of formula (2), r is 0 and one of $R_1$ and $R_2$ is a hydrogen atom while the other is a hydrocarbon group. Some examples of such organoamide compounds include N-methylbenzamide, N-ethylbenzamide, N-n-propylbenzamide (i.e., N-propylbenzamide), N-isopropylbenzamide, N-butylbenzamide, N-isobutylbenzamide, N-t-butylbenzamide, N-pentylbenzamide, N-isopentylbenzamide, N-hexylbenzamide, N-heptylbenzamide, N-octylbenzamide, N-nonylbenzamide, N-decylbenzamide, N-cyclopentylbenzamide, N-cyclohexylbenzamide, N-phenylbenzamide (benzanilide), N-benzylbenzamide, N-vinylbenzamide, N-(2-hydroxyethyl)benzamide, N-(2-aminoethyl)benzamide, and N-(2,2-dichlorovinyl)benzamide.

In another embodiment of formula (2), r is 0 and both of $R_1$ and $R_2$ are hydrocarbon groups. Some examples of such organoamide compounds include N,N-dimethylbenzamide (i.e., DMBA), N-methyl-N-ethylbenzamide, N-methyl-N-propylbenzamide, N-methyl-N-isopropylbenzamide, N-methyl-N-butylbenzamide, N-methyl-N-isobutylbenzamide, N-methyl-N-phenylbenzamide, N-methyl-N-cyclohexylbenzamide, N-methyl-N-benzylbenzamide, N,N-diethylbenzamide, N-ethyl-N-isopropylbenzamide, N-ethyl-N-butylbenzamide, N-ethyl-N-isobutylbenzamide, N-ethyl-N-phenylbenzamide, N-ethyl-N-benzylbenzamide, N,N-dipropylbenzamide, N,N-diisopropylbenzamide, N-isopropyl-N-phenylbenzamide, N,N-dibutylbenzamide, N,N-diisobutylbenzamide, N,N-dicyclohexylbenzamide, N,N-diphenylbenzamide, N,N-dibenzylbenzamide, N-(2-hydroxyethyl)-N-methylbenzamide, N-(2-hydroxyethyl)-N-ethylbenzamide, N-(2-hydroxyethyl)-N-isopropylbenzamide, N,N-bis(2-hydroxyethyl)benzamide, N-(2-aminoethyl)-N-methylbenzamide, N-(2-aminoethyl)-N-ethylbenzamide, and N-(2-aminoethyl)-N-isopropylbenzamide.

In another embodiment of formula (2), r is 1 (and thus, one $R_4$ substituent is present on the shown phenyl ring), and $R_1$ and $R_2$ are hydrogen atoms. Some examples of such organoamide compounds include the o-, m-, and p-toluamides (i.e., 2-, 3-, and 4-methylbenzamides), [1,1'-biphenyl]-4,4'-dicarboxamide, and 2-, 3-, and 4-derivatives of: ethylbenzamide (i.e., 2-ethylbenzamide, 3-ethylbenzamide, 4-ethylbenzamide), propylbenzamide, isopropylbenzamide, butylbenzamide, isobutylbenzamide, t-butylbenzamide, pentylbenzamide, (1-methylbutyl)benzamide, hexylbenzamide, heptylbenzamide, octylbenzamide, nonylbenzamide, decylbenzamide, undecylbenzamide, dodecylbenzamide, vinylbenzamide, allylbenzamide, trifluoromethylbenzamide, pentafluoroethylbenzamide, biphenylcarboxamide, pentyl(1,1'-biphenyl)-4'-carboxamide, (piperidin-4-yl)benzamide, (chloromethyl)benzamide, hydroxybenzamide, hydroxymethylbenzamide, hydroxyethylbenzamide, methoxybenzamide, ethoxybenzamide, aminobenzamide, aminomethylbenzamide, aminoethylbenzamide, fluorobenzamide, chlorobenzamide, bromobenzamide, cyanobenzamide, formylbenzamide, carboxybenzamide (e.g., terephthalic acid monoamide), and amidobenzamide (e.g., terephthalamide).

In another embodiment of formula (2), r is 2 (and thus, two $R_4$ substituents are present on the shown phenyl ring), and $R_1$ and $R_2$ are hydrogen atoms. Some examples of such organoamide compounds include 2,3-dimethylbenzamide, 2,4-dimethylbenzamide, 2,5-dimethylbenzamide, 2,6-dimethylbenzamide, 3,4-dimethylbenzamide, 3,5-dimethylbenzamide, 3,5-diethylbenzamide, 3,5-diisopropylbenzamide, 2-methyl-5-isopropylbenzamide, 3-methyl-5-isopropylbenzamide, 2,4-di(trifluoromethyl)benzamide, 3,5-di(trifluoromethyl)benzamide, 2-fluoro-4-methylbenzamide, 2-amino-4-methylbenzamide, 3-amino-4-methylbenzamide, 2-methoxy-4-methylbenzamide, 2-fluoro-4-methoxybenzamide, 2-methoxy-4-(trifluoromethyl)benzamide, 3,5-difluorobenzamide, 3,5-dichlorobenzamide, and 3,5-dibromobenzamide.

In other embodiments of formula (2), r is 3, 4, or 5 (and thus, three, four, or five $R_4$ substituents are present on the shown phenyl ring), and $R_1$ and $R_2$ are hydrogen atoms. Some examples of such organoamide compounds when r is 3 include 2,3,4-trimethylbenzamide, 2,3,5-trimethylbenzamide, 2,4,6-trimethylbenzamide, 2,6-dimethyl-4-isopropylbenzamide, 4-chloro-3,5-dimethylbenzamide, 4-fluoro-3,5-dimethylbenzamide, 3,5-dibromo-4-methylbenzamide, 3,5-dichloro-4-methylbenzamide, 3,5-difluoro-4-methylbenzamide, 3,5-difluoro-4-(trifluoromethyl)benzamide, 3,5-di(trifluoromethyl)-4-fluorobenzamide, 4-amino-3,5-dimethylbenzamide, 4-methoxy-3,5-dimethylbenzamide, 3,5-dimethoxy-4-methylbenzamide, 2,6-dimethoxy-4-methylbenzamide, 2,3,4-trifluorobenzamide, 2,3,5-trifluorobenzamide, 2,4,6-trifluorobenzamide, 2,4,6-trichlorobenzamide, and 2,4,6-tribromobenzamide. Some examples of such organoamide compounds when r is 4 or 5 include 2,3,5,6-tetramethylbenzamide, 2,3,5,6-tetrafluorobenzamide, pentamethylbenzamide, pentafluorobenzamide, 4-methoxy-2,3,5,6-tetramethylbenzamide, 4-methoxy-2,3,5,6-tetrafluorobenzamide, and 4-(trifluoromethyl)-2,3,5,6-tetrafluorobenzamide.

In another embodiment of formula (2), r is 1 (i.e., one $R_4$ substituent) and one of $R_1$ and $R_2$ is a hydrogen atom while the other is a hydrocarbon group. Some examples of such organoamide compounds include the N-methyl-, N-ethyl-, N-n-propyl-, N-isopropyl-, N-n-butyl-, N-isobutyl-, N-sec-butyl-, N-t-butyl-, N-n-pentyl-, N-isopentyl-, N-neopentyl-, N-vinyl-, N-allyl-, N-phenyl-, N-benzyl-, N-(2-propynyl)-, N-cyclopentyl-, N-cyclohexyl-, N-hydroxymethyl-, N-(2-hydroxyethyl)-, N-(2-hydroxypropyl), N-(2-hydroxybutyl), N-(2-methoxyethyl), N-(aminomethyl), and N-(2-aminoethyl) derivatives of: the 2-, 3-, and 4-isomers of methylbenzamide (i.e., 2-methylbenzamide, 3-methylbenzamide, and 4-methylbenzamide), ethylbenzamide, propylbenzamide, isopropylbenzamide, n-butylbenzamide, isobutylbenzamide, t-butylbenzamide, pentylbenzamide, hexylbenzamide, heptylbenzamide, octylbenzamide, nonylbenzamide, decylbenzamide, undecylbenzamide, dodecylbenzamide, vinylbenzamide, trifluoromethylbenzamide, pentafluoroethylbenzamide, biphenylcarboxamide, hydroxybenzamide, methoxybenzamide, ethoxybenzamide, phenoxybenzamide, aminobenzamide, aminobenzamide, fluorobenzamide, chlorobenzamide, bromobenzamide, cyanobenzamide, and terephthalamide (e.g., N-methylterephthalamide, N,N-dimethylterephthalamide, and N,N'-dimethylterephthalamide).

In another embodiment of formula (2), r is 1, and both of $R_1$ and $R_2$ are hydrocarbon groups. Some examples of such organoamide compounds include the N,N-dimethyl-, N,N-diethyl-, N,N-di-n-propyl-, N,N-diisopropyl-, N,N-di-n-butyl-, N,N-diisobutyl-, N,N-diallyl-, N,N-bis(2-hydroxyethyl)-, N-methyl-N-ethyl-, N-methyl-N-n-propyl-, N-methyl-N-isopropyl-, N-methyl-N-n-butyl-, N-methyl-N-isobutyl-, N-methyl-N-t-butyl-, N-methyl-N-benzyl-, N-ethyl-N-n-propyl-, N-ethyl-N-isopropyl-, N-ethyl-N-n-butyl-, N-ethyl-N-isobutyl-, N-ethyl-N-t-butyl-, N-ethyl-N-benzyl-, N-n-propyl-N-isopropyl-, N-n-propyl-N-n-butyl-, N-n-propyl-N-isobutyl-, N-n-propyl-N-t-butyl-, N-n-propyl-N-benzyl-, N-isopropyl-N-n-butyl-, N-isopropyl-N-isobutyl-, N-isopropyl-N-t-butyl-, N-isopropyl-N-benzyl-, N-n-butyl-N-isobutyl-, N-n-butyl-N-t-butyl-, N-n-butyl-N-benzyl-, N-isobutyl-N-t-butyl-, N-isobutyl-N-benzyl-, N-methyl-N-n-pentyl-, N-methyl-N-isopentyl-, N-ethyl-N-n-pentyl-, N-ethyl-N-isopentyl-, N-n-propyl-N-n-pentyl-, N-n-propyl-N-isopentyl-, N-isopropyl-N-n-pentyl-, N-isopropyl-N-isopentyl-, N-methyl-N-vinyl-, N-ethyl-N-vinyl-, N-methyl-N-allyl-, N-ethyl-N-allyl-N-methyl-N-(2-propynyl)-, N-methyl-N-(hydroxymethyl)-, N-methyl-N-(2-hydroxyethyl)-, N-ethyl-N-(2-hydroxyethyl)-, N-isopropyl-N-(2-hydroxyethyl)-, N-n-butyl-N-(2-hydroxyethyl)-, N-isobutyl-N-(2-hydroxyethyl)-, N-methyl-N-(2-hydroxypropyl), N-methyl-N-(2-hydroxybutyl), N-methyl-N-(2-methoxyethyl), N-methyl-N-(aminomethyl), and N-methyl-N-(2-aminoethyl) derivatives of: the 2-, 3-, and 4-isomers of methylbenzamide (i.e., 2-methylbenzamide, 3-methylbenzamide, and 4-methylbenzamide), ethylbenzamide, propylbenzamide, isopropylbenzamide, n-butylbenzamide, isobutylbenzamide, t-butylbenzamide, pentylbenzamide, hexylbenzamide, heptylbenzamide, octylbenzamide, nonylbenzamide, decylbenzamide, undecylbenzamide, dodecylbenzamide, vinylbenzamide, trifluoromethylbenzamide, pentafluoroethylbenzamide, biphenylcarboxamide, hydroxybenzamide, methoxybenzamide, ethoxybenzamide, phenoxybenzamide, aminobenzamide, aminobenzamide, fluorobenzamide, chlorobenzamide, bromobenzamide, cyanobenzamide, and terephthalamide (e.g., N,N-dimethylterephthalamide and N,N,N',N'-tetramethylterephthalamide).

In separate other embodiments of formula (2), r is 2, 3, 4, or 5, while either one of $R_1$ and $R_2$ or both of $R_1$ and $R_2$ are hydrocarbon groups. Some examples of such organoamide compounds when r is 2 include N-methyl-3,5-dimethylbenzamide, N-methyl-3,5-diethylbenzamide, N-methyl-3,5-diisopropylbenzamide, N-methyl-2-methyl-5-isopropylbenzamide, N-methyl-3,5-di(trifluoromethyl)benzamide, N-methyl-2-fluoro-4-methylbenzamide, N-methyl-2-amino-4-methylbenzamide, N-methyl-2-methoxy-4-methylbenzamide, N-methyl-2-fluoro-4-methoxybenzamide, N-methyl-3,5-difluorobenzamide, N-methyl-3,5-dichlorobenzamide, N-methyl-3,5-dibromobenzamide, N-ethyl-3,5-dimethylbenzamide, N-propyl-3,5-dimethylbenzamide, N-butyl-3,5-dimethylbenzamide, N-isobutyl-3,5-dimethylbenzamide, N,N-dimethyl-3,5-dimethylbenzamide, N,N-dimethyl-3,5-diethylbenzamide, N,N-dimethyl-3,5-diisopropylbenzamide, N,N-dimethyl-2-amino-4-methylbenzamide, N,N-dimethyl-2-methoxy-4-methylbenzamide, N,N-dimethyl-2-fluoro-4-methoxybenzamide, N,N-dimethyl-3,5-difluorobenzamide, N,N-dimethyl-3,5-dichlorobenzamide, and N,N-dimethyl-3,5-dibromobenzamide. Some examples of such organoamide compounds when r is 3 include N-methyl-2,3,5-trimethylbenzamide, N-methyl-2,4,6-trimethylbenzamide, N-methyl-2,6-dimethyl-4-isopropylbenzamide, N-methyl-4-chloro-3,5-dimethylbenzamide, N-methyl-4-fluoro-3,5-dimethylbenzamide, N-methyl-3,5-difluoro-4-methylbenzamide, N-methyl-3,5-difluoro-4-(trifluoromethyebenzamide, N-methyl-3,5-di(trifluoromethyl)-4-fluorobenzamide, N-methyl-4-amino-3,5-dimethylbenzamide, N-methyl-4-methoxy-3,5-dimethylbenzamide, N-methyl-3,5-dimethoxy-4-methylbenzamide, N-methyl-2,4,6-trifluorobenzamide, N-ethyl-2,4,6-trimethylbenzamide, N-propyl-2,3,5-trimethylbenzamide, N-butyl-2,4,6-trimethylbenzamide, N-butyl-4-methoxy-3,5-dimethylbenzamide, N,N-dimethyl-2,3,5-trimethylbenzamide, N,N-dimethyl-2,4,6-trimethylbenzamide, N,N-dimethyl-4-fluoro-3,5-dimethylbenzamide, N,N-dimethyl-3,5-difluoro-4-methylbenzamide, N,N-dimethyl-3,5-difluoro-4-(trifluoromethyl)benzamide, N,N-dimethyl-4-amino-3,5-dimethylbenzamide, N,N-dimethyl-4-methoxy-3,5-dimethylbenzamide, N,N-dimethyl-3,5-dimethoxy-4-methylbenzamide, N,N-dimethyl-2,4,6-trifluorobenzamide, N,N-diethyl-2,4,6-trimethylbenzamide, N-methyl-N-propyl-2,4,6-trimethylbenzamide, N-methyl-N-butyl-2,4,6-trimethylbenzamide, N-methyl-N-isobutyl-2,4,6-trimethylbenzamide, N-propyl-2,3,5-trimethylbenzamide, N-methyl-N-isopropyl-2,3,5-trimethylbenzamide, and N-methyl-N-butyl-4-methoxy-3,5-dimethylbenzamide.

In formula (2), $R_4$ can optionally bind to two different carbon atoms of the shown phenyl ring, thereby forming a fused ring or ring system with the shown phenyl ring. Some examples of such organoamide compounds include naphthalene-1-carboxamide (i.e., 1-naphthamide), naphthalene-2-carboxamide, 2,3-naphthalenedicarboxamide, 3-hydroxy-2-naphthamide, and 3-phenanthrenecarboxamide.

In another embodiment, the one or more neutral ligands complexed to silver (I) are selected from the class of organoamines. The organoamine compounds considered herein are the class of compounds containing at least one nitrogen atom bound to at least one carbon atom and the remainder one or more atoms, if any, bound to the nitrogen atom are hydrogen atoms. The organoamine can be a primary, secondary, or tertiary amine. In addition, the organoamine can be a monoamine, diamine, triamine, tetramine, or higher amine. Furthermore, in different embodiments, the organoamine can be a saturated amine, unsaturated amine, straight-chained amine, branched amine, cycloamine, or a combination thereof (e.g., straight-chained and saturated).

In a particular embodiment, the organoamines have a chemical formula within the following generic formula:

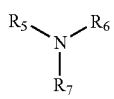

(3)

In formula (3), each of $R_5$, $R_6$, and $R_7$ is either a hydrocarbon group or hydrogen atom, wherein at least one of $R_5$, $R_6$, and $R_7$ is a hydrocarbon group. In particular embodiments of formula (3), one, two, or three hydrocarbon groups therein independently contain precisely, or a minimum of, or a maximum of, for example, one, two, three, four, five, six, seven, eight, nine, ten, eleven, twelve, thirteen, fourteen, fifteen, sixteen, seventeen, eighteen, nineteen, or twenty carbon atoms, or a particular range governed by any two of the foregoing carbon numbers. Preferably, if one or more heteroatoms are present in $R_5$, $R_6$, and/or $R_7$, the heteroatoms are not directly attached to the shown nitrogen atom.

In one embodiment of formula (3) the organoamines are primary amines, i.e., one of $R_5$, $R_6$, and $R_7$ is a hydrocarbon group while the remaining two are hydrogen atoms. Some examples of such organoamine compounds include methylamine, ethylamine (i.e., ethanamine), n-propylamine (i.e., propylamine), isopropylamine, n-butylamine (i.e., butylamine), sec-butylamine, isobutylamine, t-butylamine, n-pentylamine, isopentylamine, 2-aminopentane, 3-aminopentane, n-hexylamine, 1-amino-4-methylpentane, 1-amino-3-methylpentane, 2-aminohexane, 3-aminohexane, n-heptylamine, 1-amino-5-methylhexane, 2-aminoheptane, 3-aminoheptane, 4-aminoheptane, n-octylamine, 1-amino-6-methylheptane, 2-aminooctane, 3-aminooctane, 4-aminooctane, n-nonylamine, 1-amino-7-methyloctane, n-decylamine, 1-amino-8-methylnonane, n-undecylamine, n-dodecylamine, n-tridecylamine, tetradecylamine, pentadecylamine, hexadecylamine, heptadecylamine, octadecylamine, nonadecylamine, eicosylamine, cyclopentylamine, cyclohexylamine, ethyleneamine, allylamine, 3-buten-1-amine, 2-buten-1-amine, benzylamine, phenethylamine, aniline, o-, m-, and p-toluidine, o-, m-, and p-anisidine, o-, m-, and p-fluoroaniline, o-, m-, and p-chloroaniline, o-, m-, and p-bromoaniline, 3,5-dichloroaniline, naphthylamine, and pentafluoroaniline. Some examples of primary amines wherein the hydrocarbon group contains at least one hydroxy group include 2-hydroxyethylamine, 2-hydroxypropylamine, 3-hydroxypropylamine, 2-hydroxybutylamine, 3-hydroxybutylamine, 4-hydroxybutylamine, 2-hydroxypentylamine, 3-hydroxypentylamine, 4-hydroxypentylamine, 5-hydroxypentylamine, 2,3-dihydroxypropylamine, 2-aminophenol, 3-aminophenol, 4-aminophenol, and 5-aminobenzene-1,3-diol. Some examples of primary amines wherein the $R_5$, $R_6$, or $R_7$ hydrocarbon group contains at least one amino group include the diamines (e.g., ethylenediamine, 1,3-diaminopropane, 1,4-diaminobutane, 1,5-diaminopentane, 1,6-diaminohexane, m-phenylenediamine, and m-xylylenediamine), the triamines (e.g., diethylenetriamine), and tetramines (e.g., triethylenetetramine).

In another embodiment of formula (3) the organoamines are secondary amines, i.e., two of $R_5$, $R_6$, and $R_7$ are hydrocarbon groups and one is a hydrogen atom. Some examples of such organoamine compounds include dimethylamine, methylethylamine, diethylamine, methyl(n-propyl)amine, ethyl (n-propyl)amine, di(n-propyl)amine, methyl(isopropyl)amine, ethyl(isopropyl)amine, (n-propyl)(isopropyl)amine, diisopropylamine, methyl(n-butyl)amine, ethyl(n-butyl)amine, (n-propyl)(n-butyl)amine, (isopropyl)(n-butyl)amine, di(n-butyl)amine, methyl(isobutyl)amine, ethyl(isobutyl)amine, (n-propyl)(isobutyl)amine, (isopropyl)(isobutyl)amine, diisobutylamine, methyl(sec-butyl)amine, ethyl(sec-butyl)amine, (n-propyl)(sec-butyl)amine, (isopropyl)(sec-butyl)amine, di(sec-butyl)amine, methyl(t-butyl)amine, ethyl(t-butyl)amine, (n-propyl)(t-butyl)amine, (isopropyl)(t-butyl)amine, (isobutyl)(t-butyl)amine, di-t-butylamine, methylpentylamine, ethylpentylamine, isopropylpentylamine, di-(n-pentyl)amine, diisopentylamine, methylisopentylamine, methylhexylamine, methylallylamine, diallylamine, and methylbenzylamine. Some examples of secondary amines wherein at least one of the hydrocarbon groups contains at least one hydroxy group or at least one alkoxy group include (2-hydroxyethyl)methylamine, (2-hydroxyethyl)isopropylamine, bis-(2-hydroxyethyl)amine, (2-hydroxypropyl)methylamine, (3-hydroxypropyl)methylamine, 2-hydroxybutylamine, 3-hydroxybutylamine, 4-hydroxybutylamine, (2-methoxyethyl)methylamine, bis-(2-methoxyethyl)amine, (2-methoxypropyl)methylamine, and (3-methoxypropyl)methylamine. Some examples of secondary amines wherein the hydrocarbon group contains at least one amino group include N-methylethylenediamine, N,N'-dimethylethylenediamine, N-methyl-1,3-diaminopropane, diethylenetriamine, and triethylenetetramine. Other examples of such secondary amines include, for example, the N-methyl-, N-ethyl-, N-propyl-, N-isopropyl-, N-n-butyl-, N-isobutyl-, N-t-butyl, N-n-pentyl-, N-isopentyl-, N-neopentyl-, N-benzyl-, N-vinyl-, N-hydroxymethyl-, N-(2-hydroxyethyl)-, N-(2-hydroxypropyl)-, N-(3-hydroxypropyl)-, N-(2-hydroxybutyl)-, N-(3-hydroxybutyl)-, N-(4-hydroxybutyl)-, N-aminomethyl-, N-(2-aminoethyl)-, N-(3-aminopropyl)-, N-(2-methoxyethyl)-derivatives of: aniline, o-, -m-, and -p-toluidine; o-, m-, and p-fluoroaniline; o-, m-, and p-chloroaniline; o-, m-, and p-bromoaniline; o-, m-, and p-aminophenol; o-, m-, and p-anisidine; 5-aminobenzene-1,3-diol, m-phenylenediamine, and m-xylylenediamine.

In another embodiment of formula (3) the organoamines are tertiary amines, i.e., all of $R_5$, $R_6$, and $R_7$ are hydrocarbon groups. Some examples of such organoamine compounds include trimethylamine, dimethylethylamine, methyldiethylamine, dimethyl(n-propyl)amine, diethyl(n-propyl)amine, di-(n-propyl)methylamine, tri(n-propyl)amine, dimethyl (isopropyl)amine, diethyl(isopropyl)amine, diisopropylmethylamine, triisopropylamine, dimethyl(n-butyl)amine, diethyl(n-butyl)amine, di(n-butyl)methylamine, di(isopropyl)(n-butyl)amine, tri(n-butyl)amine, dimethyl(isobutyl)amine, diethyl(isobutyl)amine, di(isopropyl)(isobutyl)amine, di(isobutyl)methylamine, di(isobutyl)ethylamine, triisobutylamine, dimethyl(t-butyl)amine, diethyl(t-butyl)amine, di(t-butyl)methylamine, di(t-butyl)ethylamine, tri-t-butylamine, dimethylpentylamine, diethylpentylamine, dimethylisopentylamine, dimethylhexylamine, dimethylallylamine, diallylmethylamine, dimethylbenzylamine, N,N-dimethylaniline, and N,N-dimethyl-derivatives of: o-, -m-, and -p-toluidine, o-, m-, and p-fluoroaniline, o-, m-, and p-chloroaniline, and o-, m-, and p-bromoaniline. Some examples of tertiary amines wherein at least one of the hydrocarbon groups contains at least one hydroxy or alkoxy group include (2-hydroxyethyl)dimethylamine, bis(2-hydroxyethyl)methylamine, tris(2-hydroxyethyl)amine, (2-hydroxypropyl)dimethylamine, (2-hydroxypropyl)diethylamine, bis(2-hydroxypropyl)methylamine, and N,N-dimethyl-derivatives of: 2-aminophenol, 3-aminophenol, 4-aminophenol, and o-, m-, and p-anisidine. Some examples of tertiary amines wherein the hydrocarbon group contains at least one amino group include N,N-dimethylethylenediamine and N,N,N',N'-tetramethylethylenediamine (TMEDA).

In one embodiment of formula (3), when at least two of $R_5$, $R_6$, and $R_7$ are hydrocarbon groups, the hydrocarbon groups may crosslink such that an amino-containing cyclic ring results (i.e., two of $R_5$, $R_6$, and $R_7$ may combine to form a ring structure). In another embodiment, $R_5$, $R_6$, and $R_7$ are not allowed to combine to form a ring structure. Some examples of amines which include at least one amino group in a ring structure include pyrrole, pyrrolidine, imidazole, pyrazole, indole, piperidine, pyridine, piperazine, pyrazine, oxazole, purine, pyrimidine, benzimidazole, bipyridine, and their N-methyl-, N-ethyl-, N-propyl-, N-isopropyl-, N-n-butyl-, N-isobutyl-, N-t-butyl, N-pentyl-, N-phenyl, N-benzyl, N-vinyl, and N-allyl derivatives.

In another embodiment, the one or more neutral ligands complexed to silver (I) are selected from the class of olefins. The olefin compounds considered herein are the class of compounds containing at least one carbon-carbon double bond. The olefin can contain, for example, one, two, three, or four carbon-carbon double bonds. In different embodiments, the olefin can contain precisely, or a minimum of, or a maximum of, for example, two, three, four, five, six, seven, eight, nine, ten, eleven, twelve, thirteen, fourteen, fifteen, sixteen, seventeen, or eighteen carbon atoms, or a particular range of carbon atoms between any of the foregoing carbon numbers. The olefin can also be an end-olefin, an internal olefin, or a combination thereof. An internal olefin can have either a cis or trans orientation. In addition, the olefin can contain one or more, or all, of the carbon atoms as primary, secondary, or tertiary carbon atoms. Furthermore, in different embodiments, the olefin may be straight-chained, or branched, or include a cyclic group, or exclude a cyclic group (or more specifically, exclude an olefinic ring or a phenyl ring).

In one embodiment, the olefin is straight-chained. Some examples of suitable straight-chained olefins include ethylene, propene, 1-butene, 2-butene, 1-pentene, 2-pentene, 1-hexene, 2-hexene, 3-hexene, 1-heptene, 2-heptene, 3-heptene, 1-octene, 2-octene, 3-octene, 4-octene, 1-nonene, 2-nonene, 3-nonene, 4-nonene, 1-decene, 2-decene, 3-decene, 4-decene, 5-decene, 1-undecene, 1-dodecene, 2-dodecene, 1-tridecene, 1-tetradecene, 1-pentadecene, 1-hexadecene, 1-heptadecene, 1-octadecene, 2-octadecene, 3-octadecene, 4-octadecene, butadiene, 1,4-pentadiene, 1,3-pentadiene, 1,3-hexadiene, 1,4-hexadiene, 1,5-hexadiene, 1,3,5-hexatriene, 1,3-heptadiene, 2,4-heptadiene, 1,4-heptadiene, 1,5-heptadiene, 1,6-heptadiene, 1,3,5-heptatriene, 1,3-octadiene, 1,4-octadiene, 1,5-octadiene, 1,6-octadiene, 1,7-octadiene, 2,4-octadiene, 2,6-octadiene, 1,3,5-octatriene, 2,4,6-octatriene, 1,4,6-octatriene, 1,4,7-octatriene, and 1,3,5,7-octatetraene.

In another embodiment, the olefin is branched. Some examples of branched olefins include 2-methylpropene (isobutene), isoprene, 2-methyl-1-butene, 2-methyl-2-butene, 3-methyl-1-butene (isopentene), 2-methyl-1-pentene, 3-methyl-1-pentene, 4-methyl-1-pentene, 2-methyl-2-pentene, 3-methyl-2-pentene, 4-methyl-2-pentene, 2,3-dimethylbutadiene, 2-methyl-1,4-pentadiene, 2,4-dimethyl-1,4-pentadiene, 2-methyl-1-hexene, 2,5-dimethyl-2,4-hexadiene, 2-methyl-1-octene and 2-methyl-2-decene.

In another embodiment, the olefin includes a cyclic moiety. Some examples of suitable cyclic olefins include cyclobutene, cyclopentene, cyclohexene, benzene, 1-methylcyclopentene, 1,2-dimethylcyclopentene, 1-methylcyclohexene, 1,2-dimethylcyclohexene, 4-methylcyclopent-1-ene, 5-methylcyclopenta-1,3-diene, cyclopentadiene, 1,3-cyclohexadiene, 1,4-cyclohexadiene, toluene, o-xylene, m-xylene, p-xylene, methylenecyclohexane, stilbene (E or Z), styrene, divinylbenzene, vinylcyclohexane, vinylcyclopentane, and naphthalene.

In another embodiment, the one or more neutral ligands complexed to silver (I) are selected from the class of organonitriles. The organonitrile compounds considered herein are the class of compounds containing at least one cyanide (i.e., CN) group. The organonitrile can contain, for example, one, two, or three CN groups. In different embodiments, the organonitrile can contain precisely, or a minimum of, or a maximum of, for example, one, two, three, four, five, six, seven, eight, nine, ten, eleven, twelve, thirteen, fourteen, fifteen, sixteen, seventeen, or eighteen carbon atoms, excluding the carbon atoms associated with the one or more CN groups. The organonitriles may also desirably contain a particular range of carbon atoms between any of the foregoing carbon numbers. The organonitriles may also contain one or more heteroatom-containing groups, aside from the one or more cyano groups, as described above for the hydrocarbon groups. Preferably, if one or more heteroatoms (besides the one or more cyanide groups) are present in the organonitrile compound, the one or more heteroatoms are not directly attached to a cyanide group of the organonitrile compound.

In one embodiment, the carbon atoms of the organonitrile, other than the cyanide groups, are saturated. Such organonitrile compounds can also be either straight-chained, branched, or cyclic. Some examples of saturated straight-chained organonitrile compounds include acetonitrile, trifluoroacetonitrile, propionitrile, butyronitrile, valeronitrile (pentanenitrile), capronitrile (hexanenitrile), heptanenitrile, octanenitrile, nonanenitrile, decanenitrile, undecanenitrile, dodecanenitrile, tridecanenitrile, tetradecanenitrile, pentadecanenitrile, hexadecanenitrile, heptadecanenitrile, octadecanenitrile, glycolonitrile (2-hydroxyacetonitrile), cyanoacetic acid, 2-cyanoethylether, 2-hydroxypropionitrile, 2-aminopropionitrile, 3-hydroxybutyronitrile, and 3-aminobutyronitrile. Some examples of saturated branched organonitrile compounds include isobutyronitrile (2-methylpropanenitrile), 2-methylbutyronitrile, 3-methylbutyronitrile, pivalonitrile (trimethylacetonitrile), 2-ethylbutanenitrile (diethylacetonitrile), 3,3-dimethylbutyronitrile, and 5-methylhexanenitrile. Some examples of saturated cyclic organonitrile compounds include cyclopentanecarbonitrile, cyclohexanecarbonitrile, and 4-fluorocyclohexanecarbonitrile. Some examples of saturated organonitrile compounds containing two cyanide groups include malononitrile (propanedinitrile or 1,3-dicyanopropane), succinonitrile (butanedinitrile), glutaronitrile, adiponitrile, pimelonitrile (1,5-dicyanopentane), suberonitrile (1,6-dicyanohexane), azelaic dinitrile (1,7-dicyanoheptane or azelanitrile), sebaconitrile (1,8-dicyanooctane), 1,9-dicyanononane, 1,10-dicyanodecane, 1,11-dicyanoundecane, 1,12-dicyanododecane, 1,13-dicyanotridecane, 1,14-dicyanotetradecane, 1,15-dicyanopentadecane, 1,16-dicyanohexadecane, 1,17-dicyanoheptadecane, and 1,18-dicyanooctadecane.

In another embodiment, at least a portion of the carbon atoms of the organonitrile, other than the cyanide groups, are unsaturated. Such organonitrile compounds can also be either straight-chained, branched, or cyclic. Some examples of unsaturated straight-chained organonitrile compounds include allylnitrile, acrylonitrile, 3-methoxyacrylonitrile, 2-chloroacrylonitrile, 2-butenenitrile (crotononitrile), 3-aminocrotononitrile, 3-butenenitrile, 2-pentenenitrile, 3-pentenenitrile, 4-pentenenitrile, 5-hexenenitrile, 5-heptenenitrile, 6-heptenenitrile, 6-octenenitrile, 7-octenenitrile, and 2,4-pentadienenitrile. Some examples of unsaturated branched organonitrile compounds include methacrylonitrile, 2-methyl-2-butenenitrile, 3-methyl-2-butenenitrile, 2-methyl-3-butenenitrile, 3-methyl-3-butenenitrile, 2-methyl-4-pentenenitrile, 3-methyl-4-pentenenitrile, 4-methylpentenenitrile, 2-methyl-2,4-pentadienenitrile, 5-methyl-5-hexenenitrile, 3,5-dimethyl-5-hexenenitrile, 7-methyl-7-octenenitrile, and 3,7-dimethyl-2,6-octadienenitrile. Some examples of unsaturated cyclic organonitrile compounds include benzonitrile, phenylacetonitrile (benzyl cyanide), cinnamonitrile, 4-methoxycinnamonitrile, 4-dimethylaminocinnamonitrile, 1-cyclopenteneacetonitrile, 1-cyclohexenylacetonitrile, and naphthonitrile. Some examples of unsaturated organonitrile compounds containing two or more cyanide groups include phthalonitrile (1,2-dicyanobenzene), isophthalonitrile (1,3-dicyanobenzene), terephthalonitrile (1,4-dicyanobenzene), 1,2-dicyanoethylene (e.g., fumaronitrile), 1,2-dicyanoacetylene (i.e., 2-butynedinitrile), 4-aminophthalonitrile, 2-(trifluoromethyl)terephthalonitrile, 4-methylphthalonitrile, 2,6-dicyanotoluene, 2,3-dicyanotoluene, 2,4-dicyanotoluene, 3,5-dicyanotoluene, 1,4-dicyano-2-butene, 4-(4-cyanophenyl)benzonitrile, 4,4'-dicyanobibenzyl, 2,3-dicyanohydroquinone, 2,3-naphthalenedicarbonitrile, 4,5-dicyanoimidazole, 2,4-dicyanopyridine, 2,3-dicyanopyridine, 2,3-dicyanopyrazine, 2,3-dicyanofuran, benzylidenemalononitrile, 1-propene-1,1,3-tricarbonitrile, 2-amino-1-propene-1,1,3-tricarbonitrile, tetracyanoethylene, and 7,7,8,8-tetracyanoquinodimethane.

In a particular embodiment, the one or more organonitrile compounds have chemical formulae within the following generic chemical formula:

$$R_8\text{—}(CN)_t \qquad (4)$$

wherein subscript t is 1 or 2 to indicate the presence of 1 or 2 cyanide groups, respectively, and $R_8$ is a hydrocarbon group (when t is 1) or a hydrocarbon linker (when t is 2) containing at least one and up to six, seven, or eight carbon atoms. In a more specific embodiment, $R_8$ is an alkyl group or alkylene linker containing at least one and up to six, seven, or eight carbon atoms.

The anionic portion of the ionic liquid preferably has a formula within the following generic formula:

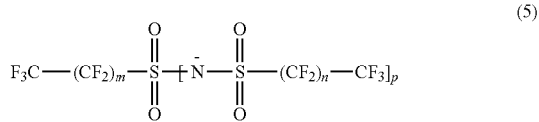

(5)

In formula (5) above, subscripts m and n are independently 0 or an integer of 1 or above. Subscript p is 0 or 1, provided that when p is 0, the group —N—$SO_2$—$(CF_2)_n CF_3$ subtended by p is replaced with an oxide atom connected to the sulfur atom (S). However, when the neutral ligand is N,N-dimethylbenzamide, or saturated primary amines containing up to four carbon atoms, or olefins containing up to six carbon atoms, m and n are preferably not both 0. More preferably, m and n are not 0 when the neutral ligand is N,N-dimethylbenzamide, or saturated primary amines containing up to four carbon atoms, or olefins selected from 1-pentene, 1-hexene, and isoprene.

In one embodiment, subscript p is 1, so that formula (5) reduces to the chemical formula:

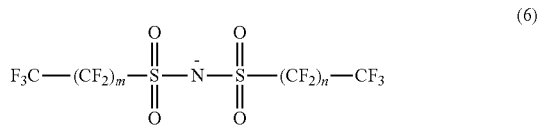

(6)

In one embodiment of formula (6), the shown perfluoroalkyl groups do not crosslink with each other, thereby resulting in a non-cyclic anion. In one case, m and n are the same number, thereby resulting in a symmetrical counteranion. In another case, m and n are not the same number, thereby resulting in an asymmetrical counteranion.

In a first set of embodiments of formula (6), m and n are independently at least 0 and up to 1, 2, 3, 4, 5, 6, 7, 8, 9, 10, or 11. When m and n are both 0, the resulting anion has the formula $F_3CSO_2NSO_2CF_3$, i.e., bis-(trifluoromethylsulfonyl)imide, or $Tf_2H^-$. In another embodiment, m and n are not both 0. For example, in a particular embodiment, m is 0 while n is a value of 1 or above (e.g., 1, 2, 3, 4, 5, 6, 7, 8, 9, 10, or 11). Some examples of such anions include $F_3CSO_2NSO_2CF_2CF_3$, $F_3CSO_2NSO_2(CF_2)_2CF_3$, $F_3CSO_2NSO_2(CF_2)_3CF_3$, $F_3CSO_2NSO_2(CF_2)_4CF_3$, $F_3CSO_2NSO_2(CF_2)_5CF_3$, and so on, wherein it is understood that, in the foregoing examples, the negative sign indicative of a negative charge (i.e., "−") in the anion has been omitted for the sake of clarity.

In a second set of embodiments of formula (6), m and n are independently at least 1 and up to 2, 3, 4, 5, 6, 7, 8, 9, 10, or 11. For example, in a particular embodiment, m is 1 while n is a value of 1 or above (e.g., 1, 2, 3, 4, 5, 6, 7, 8, 9, 10, or 11). Some examples of such anions include $N[SO_2CF_2CF_3]_2$ (i.e., "BETI$^-$"), $F_3CF_2CSO_2NSO_2(CF_2)_2CF_3$, $F_3CF_2CSO_2NSO_2(CF_2)_3CF_3$, $F_3CF_2CSO_2NSO_2(CF_2)_4CF_3$, $F_3CF_2CSO_2NSO_2(CF_2)_5CF_3$, and so on.

In a third set of embodiments of formula (6), m and n are independently at least 2 and up to 3, 4, 5, 6, 7, 8, 9, 10, or 11. For example, in a particular embodiment, m is 2 while n is a value of 2 or above (e.g., 2, 3, 4, 5, 6, 7, 8, 9, 10, or 11). Some examples of such anions include $N[SO_2(CF_2)_2CF_3]_2$, $F_3C(F_2C)_2SO_2NSO_2(CF_2)_3CF_3$, $F_3C(F_2C)_2SO_2NSO_2(CF_2)_4CF_3$, $F_3C(F_2C)_2SO_2NSO_2(CF_2)_5CF_3$, and so on.

In a fourth set of embodiments of formula (6), m and n are independently at least 3 and up to 4, 5, 6, 7, 8, 9, 10, or 11. For example, in a particular embodiment, m is 3 while n is a value of 3 or above (e.g., 3, 4, 5, 6, 7, 8, 9, 10, or 11). Some examples of such anions include $N[SO_2(CF_2)_3CF_3]_2$, $F_3C(F_2C)_3SO_2NSO_2(CF_2)_4CF_3$, $F_3C(F_2C)_3SO_2NSO_2(CF_2)_5CF_3$, $F_3C(F_2C)_3SO_2NSO_2(CF_2)_6CF_3$, $F_3C(F_2C)_3SO_2NSO_2(CF_2)_7CF_3$, and so on.

In a fifth set of embodiments of formula (6), m and n are independently at least 4 and up to 5, 6, 7, 8, 9, 10, or 11. For example, in a particular embodiment, m is 4 while n is a value of 4 or above (e.g., 4, 5, 6, 7, 8, 9, 10, or 11). Some examples of such anions include $N[SO_2(CF_2)_4CF_3]_2$, $F_3C(F_2C)_4SO_2NSO_2(CF_2)_5CF_3$, $F_3C(F_2C)_4SO_2NSO_2(CF_2)_6CF_3$, $F_3C(F_2C)_4SO_2NSO_2(CF_2)_7CF_3$, $F_3C(F_2C)_4SO_2NSO_2(CF_2)_8CF_3$, and so on.

In a sixth set of embodiments of formula (6), m and n are independently at least 5 and up to 6, 7, 8, 9, 10, or 11. For example, in a particular embodiment, m is 5 while n is a value of 5 or above (e.g., 5, 6, 7, 8, 9, 10, or 11). Some examples of such anions include $N[SO_2(CF_2)_5CF_3]_2$, $F_3C(F_2C)_5SO_2NSO_2(CF_2)_6CF_3$, $F_3C(F_2C)_5SO_2NSO_2(CF_2)_7CF_3$, $F_3C(F_2C)_5SO_2NSO_2(CF_2)_8CF_3$, $F_3C(F_2C)_5SO_2NSO_2(CF_2)_9CF_3$, and so on.

In a seventh set of embodiments of formula (6), m and n are independently at least 6 and up to 7, 8, 9, 10, or 11. For example, in a particular embodiment, m is 6 while n is a value of 6 or above (e.g., 6, 7, 8, 9, 10, or 11). Some examples of such anions include $N[SO_2(CF_2)_6CF_3]_2$, $F_3C(F_2C)_6SO_2NSO_2(CF_2)_7CF_3$, $F_3C(F_2C)_6SO_2NSO_2(CF_2)_8CF_3$, $F_3C(F_2C)_6SO_2NSO_2(CF_2)_9CF_3$, $F_3C(F_2C)_6SO_2NSO_2(CF_2)_{10}CF_3$, and so on.

In an eighth set of embodiments of formula (6), m and n are independently at least 7 and up to 8, 9, 10, or 11. For example, in a particular embodiment, m is 7 while n is a value of 7 or above (e.g., 7, 8, 9, 10, or 11). Some examples of such anions include N[SO$_2$(CF$_2$)$_7$CF$_3$]$_2$, F$_3$C(F$_2$C)$_7$SO$_2$NSO$_2$(CF$_2$)$_8$CF$_3$, F$_3$C(F$_2$C)$_7$SO$_2$NSO$_2$(CF$_2$)$_9$CF$_3$, F$_3$C(F$_2$C)$_7$SO$_2$NSO$_2$(CF$_2$)$_{10}$CF$_3$, and F$_3$C(F$_2$C)$_7$SO$_2$NSO$_2$(CF$_2$)$_{11}$CF$_3$.

In other embodiments of formula (6), m abides by one or a number of alternative conditions set forth in one of the foregoing eight embodiments while n abides by one or a number of alternative conditions set forth in another of the foregoing eight embodiments.

In yet another embodiment of formula (6), the two fluoroalkyl chains shown therein are crosslinked to form a cyclic anion structure (i.e., along with removal of two fluorine atoms). In a particular embodiment, the cyclic anion has a formula within the following generic formula:

(7)

In formula (7) above, subscript v preferably has a value of 0, 1, or 2, to produce, respectively, a five-membered, six-membered, or seven-membered ring. Though formula (7) is shown as an unbranched and saturated cyclic system containing difluoromethylene units, the cyclic anion can also be branched (e.g., by the presence of —CH$_3$ or CF$_3$ groups) and/or unsaturated (e.g., by the presence of a —CF═CF— group).

In another embodiment, subscript p in formula (5) is 0, so that formula (5) reduces to the chemical formula:

(8)

In different exemplary embodiments of formula (8), m can be 0 or above (e.g., up to 1, 2, 3, 4, 5, 6, 7, 8, 9, 10, or 11), 1 or above (e.g., up to 2, 3, 4, 5, 6, 7, 8, 9, 10, or 11), 2 or above (e.g., up to 3, 4, 5, 6, 7, 8, 9, 10, or 11), 3 or above (e.g., up to 4, 5, 6, 7, 8, 9, 10, or 11), 4 or above (e.g., up to 5, 6, 7, 8, 9, 10, or 11), 5 or above (e.g., up to 6, 7, 8, 9, 10, or 11), 6 or above (e.g., up to 7, 8, 9, 10, or 11), 7 or above (e.g., up to 8, 9, 10, 11, or 12), 8 or above (e.g., up to 9, 10, 11, or 12), or 9 or above (e.g., up to 10, 11, 12, 13, 14, 15, or 16). Some examples of such anions include F$_3$CSO$_3$$^-$ (i.e., "triflate" or "TfO$^-$"), F$_3$CF$_2$CSO$_3$$^-$, F$_3$C(F$_2$C)$_2$SO$_3$$^-$, F$_3$C(F$_2$C)$_3$SO$_3$$^-$ (i.e., "nonaflate" or "NfO$^-$"), F$_3$C(F$_2$C)$_4$SO$_3$$^-$, F$_3$C(F$_2$C)$_5$SO$_3$$^-$, F$_3$C(F$_2$C)$_6$SO$_3$$^-$, F$_3$C(F$_2$C)$_7$SO$_3$$^-$, F$_3$C(F$_2$C)$_8$SO$_3$$^-$, F$_3$C(F$_2$C)$_9$SO$_3$$^-$, F$_3$C(F$_2$C)$_{10}$SO$_3$$^-$, F$_3$C(F$_2$C)$_{11}$SO$_3$$^-$, and so on.

In a particular embodiment, the cationic portion of the ionic liquid is a complex of Ag$^+$ and saturated primary amines, denoted generically according to the formula:

(9)

In formula (9), R and R' are each independently a saturated and either straight-chained or branched hydrocarbon group containing 1, 2, 3, or 4 carbon atoms. R and R' can be selected from, for example, methyl (Me), ethyl (Et), n-propyl (n-Pr), isopropyl (i-Pr), n-butyl (n-Bu), isobutyl (i-Bu), sec-butyl (sec-Bu), and t-butyl (t-Bu) groups. In a particular embodiment, R and R' are equivalent, thereby resulting in a symmetric silver-amine complex. Some examples of such silver complexes include Ag$^+$(MeNH$_2$)$_2$, Ag$^+$(EtNH$_2$)$_2$, Ag$^+$(n-PrNH$_2$)$_2$, Ag$^+$(i-PrNH$_2$)$_2$, Ag$^+$(n-BuNH$_2$)$_2$, Ag$^+$(i-BuNH$_2$)$_2$, Ag$^+$(sec-BuNH$_2$)$_2$, and Ag$^+$(t-BuNH$_2$)$_2$. In another particular embodiment, R and R' are different, thereby resulting in an asymmetric silver-amine complex. Some examples of such silver complexes include Ag$^+$(MeNH$_2$)(EtNH$_2$), Ag$^+$(MeNH$_2$)(n-PrNH$_2$), Ag$^+$(MeNH$_2$)(i-PrNH$_2$), Ag$^+$(MeNH$_2$)(n-BuNH$_2$), Ag$^+$(MeNH$_2$)(i-BuNH$_2$), Ag$^+$(MeNH$_2$)(sec-BuNH$_2$), Ag$^+$(MeNH$_2$)(t-BuNH$_2$), Ag$^+$(EtNH$_2$)(n-PrNH$_2$), Ag$^+$(EtNH$_2$)(i-PrNH$_2$), Ag$^+$(EtNH$_2$)(n-BuNH$_2$), Ag$^+$(EtNH$_2$)(i-BuNH$_2$), Ag$^+$(EtNH$_2$)(sec-BuNH$_2$), Ag$^+$(EtNH$_2$)(t-BuNH$_2$), Ag$^+$(n-PrNH$_2$)(i-PrNH$_2$), Ag$^+$(n-PrNH$_2$)(n-BuNH$_2$), Ag$^+$(n-PrNH$_2$)(i-BuNH$_2$), Ag$^+$(n-PrNH$_2$)(sec-BuNH$_2$), Ag$^+$(n-PrNH$_2$)(t-BuNH$_2$), Ag$^+$(i-PrNH$_2$)(n-BuNH$_2$), Ag$^+$(i-PrNH$_2$)(i-BuNH$_2$), Ag$^+$(i-PrNH$_2$)(sec-BuNH$_2$), Ag$^+$(i-PrNH$_2$)(t-BuNH$_2$), Ag$^+$(n-BuNH$_2$)(i-BuNH$_2$), Ag$^+$(n-BuNH$_2$)(sec-BuNH$_2$), Ag$^+$(n-BuNH$_2$)(t-BuNH$_2$), Ag$^+$(i-BuNH$_2$)(sec-BuNH$_2$), Ag$^+$(i-BuNH$_2$)(t-BuNH$_2$), and Ag$^+$(sec-BuNH$_2$)(t-BuNH$_2$).

The ionic liquids of the invention contain any of the Ag$^+$-neutral ligand cations described above complexed to any of the anions described above (e.g., as in formulas 5-8) in a molar ratio which maintains charge neutrality (typically, a 1:1 molar ratio). Some examples of ionic liquid compositions according to the invention include Ag(DMBA)$_2$$^+$BETI$^-$, Ag(1-pentene)$^+$BETI$^-$, Ag(1-hexene)$^+$BETI$^-$, Ag(1-isoprene)$^+$BETI$^-$, Ag(DMBA)$_2$$^+$TfO$^-$, Ag(1-pentene)$^+$TfO$^-$, Ag(1-hexene)$^+$TfO$^-$, Ag(isoprene)$^+$TfO$^-$, Ag(DMBA)$_2$$^+$NfO$^-$, Ag(1-pentene)$^+$NfO$^-$, Ag(1-hexene)$^+$NfO$^-$, and Ag(isoprene)$^+$NfO$^-$.

The ionic liquids of the invention are preferably in liquid form (i.e., fluids) at or below 100° C., more preferably at or below 50° C., and even more preferably, at or below room temperature (i.e., at or less than about 15, 20, 25, or 30° C.). In other embodiments, the ionic liquids are in liquid form at or below 0° C., −5° C., −10° C., −20° C., or −30° C. Preferably, the ionic liquid possesses a melting point which is at or below any of the temperatures given above. Though the invention primarily contemplates ionic liquids that are naturally fluids at or below room temperature, the invention also contemplates ionic liquids that are solid or semi-solid at about room temperature or above, but which can be rendered liquids at a higher temperature by the application of heat. The latter embodiment may be particularly suitable if the process in which the ionic liquid is used is a high temperature process (i.e., above room temperature).

The density of the ionic liquid is generally above 1.2 g/mL at an operating temperature of interest, and particularly at a temperature within 20-30° C. In different embodiments, the density of the ionic liquid is preferably at least 1.2, 1.3, 1.4, 1.5, 1.6, 1.7, or 1.8 g/mL, or a particular range between any two of these values.

The viscosity of the ionic liquid is preferably no more than 50,000 centipoise (50,000 cP) at an operating temperature of interest, and particularly at a temperature within 20-30° C. In more preferred embodiments, the viscosity of the ionic liquid is no more than about 25,000 cP, 10,000 cP, 5,000 cP, 2,000 cP, 1,000 cP, 800 cP, 700 cP, 600 cP, 500 cP, 400 cP, 300 cP, 200 cP, 120 cP, 100 cP, or 50 cP. Alternatively, the viscosity of the ionic liquid may preferably be within a particular range established between any two of the foregoing exemplary values.

The conductivity of the ionic liquid is preferably at least 0.01 mS/cm (0.001 S/m) at an operating temperature of interest, and particularly at a temperature within 20-30° C. In different embodiments, the conductivity of the ionic liquid may preferably be at least 0.01, 0.05, 0.1, 0.2, 0.3, 0.4, 0.5, 1.0, 2.0, 3.0, 4.0, 5.0, 6.0, 7.0, 8.0, 9.0, 10.0, 11.0. or 12.0 mS/cm, or a particular range between any two of the foregoing values.

In another aspect, the invention is directed to applying the above-described ionic liquids to an olefin-paraffin separation process. The use of separation membranes is well known in the art of olefin-paraffin separation processes. As known in the art, the ionic liquid is typically in the form of a membrane which is permeable to the olefin-paraffin gaseous mixture. The membrane typically includes a layer of the ionic liquid on a suitable gas-permeable substrate (i.e., support). The layer may also be sandwiched between two layers of the support material. The support is preferably composed of a material which is inert, i.e., non-reactive and non-adsorptive to the olefin or paraffin gases, or to the ionic liquids. The ionic liquid may also be integrated (i.e., impregnated or infused) within the support material. Some examples of support materials include alumina, silica, metal oxides, and polymers (e.g., organic, inorganic, or hybrid). The layer of ionic liquid can have any suitable thickness, typically at least 1, 2, 3, 4, 5, 6, 7, or 8 microns and up to 10, 20, or 30 microns. When the olefin-paraffin gaseous mixture is passed through the ionic liquid membrane, the ionic liquid selectively transports the olefin through the membrane by silver complexation, thereby separating the mixture.

In one embodiment, the ionic liquid is admixed with one or more solvents. The solvent can be, for example, a polar protic solvent, polar non-protic solvent, or a non-polar solvent. Some examples of polar protic solvents include the alcohols containing up to four linked carbon atoms (e.g., methanol, ethanol, isopropanol, n-butanol, t-butanol), diols (e.g., ethylene glycol, diethylene glycol, triethylene glycol), and protic amines (e.g., ethylenediamine, ethanolamine, diethanolamine, triethanolamine). Some examples of polar non-protic solvents include the nitriles (e.g., acetonitrile, propionitrile), sulfoxides (e.g., dimethylsulfoxide), amides (e.g., dimethylformamide, N,N-dimethylacetamide), organochlorides (e.g., methylene chloride, chloroform, 1,1,-trichloroethane), ketones (e.g., acetone, 2-butanone), dialkylcarbonates (e.g., ethylene carbonate, dimethylcarbonate, diethylcarbonate), organoethers (e.g., diethyl ether, tetrahydrofuran, and dioxane), HMPA, NMP, and DMPU. As used herein, a "non-polar solvent" is a solvent containing a linkage of at least five carbon atoms. Accordingly, some examples of non-polar solvents include n-pentanol, n-hexanol, a pentane, hexane, heptane, octane, pentene, hexene, heptene, octene, or an aromatic solvent, such as benzene, toluene, or a xylene. In different embodiments, the solvent can be included in an amount of, or at least, or less than, for example, 0.1 wt %, 0.5 wt %, 10 wt %, 20 wt %, 30 wt %, 40 wt %, 50 wt %, 60 wt %, 70 wt %, 80 wt %, 90 wt % (by total weight of the ionic liquid, solvent, and any other components), or a range between any of these values.

In other embodiments, one or more of any of the foregoing classes of solvents, or specific solvents, is excluded. For example, in some embodiments, it may be preferable to exclude solvents having a boiling point over 25° C., 50° C., or 100° C. In other embodiments, it may be preferable to exclude solvents having a boiling point under 25° C., 50° C., or 100° C. In yet other embodiments, it may preferable to include only one or more solvents in which the ionic liquid is substantially soluble, or partially soluble, or substantially insoluble (e.g., as separate phases). In a particular embodiment, all solvents are excluded.

Preferably, the ionic liquid is substantially devoid of water. In preferred embodiments, it is desirable that the ionic liquid contains less than 1% by weight of water, and more preferably, less than 0.5%, 0.1%, 0.01%, or even 0.001% by weight of water. The ionic liquid is also preferably substantially devoid of salt byproducts (e.g., $LiNO_3$) that are typically produced during synthesis of the ionic liquid. In preferred embodiments, it is desirable that the ionic liquid contains less than 1% by weight of salt byproducts, and more preferably, less than 0.5%, 0.1%, 0.01%, or even 0.001% by weight of salt byproducts.

The olefin in the olefin-paraffin mixture is typically any of the olefins described above which contain up to six, seven, or eight carbon atoms. Some common examples of olefins in the mixture include propene, 2-methylpropene, 1-butene, 2-butene, 2-methyl-1-butene, 3-methyl-1-butene, 2-methyl-2-butene, 2,3-dimethyl-2-butene, 1-pentene, 2-pentene, 2-methyl-1-pentene, 3-methyl-1-pentene, 4-methyl-1-pentene, 2-methyl-2-pentene, 1-hexene, 2-hexene, 3-hexene, 2-methyl-1-hexene, 1-heptene, 1-octene, isoprene, butadiene, cyclopentene, and cyclohexene.

The paraffin in the olefin-paraffin mixture can be a straight-chained, branched, or cyclic alkane, typically containing up to six carbon atoms (e.g., 2, 3, 4, 5, or 6 carbon atoms, or a range therebetween). Some common examples of such paraffins include, for example, propane, n-butane, isobutane, n-pentane, isopentane, neopentane, n-hexane, isohexane, 3-methylpentane, 2,3-dimethylbutane, 2,2-dimethylbutane, cyclopentane, and cyclohexane. Typically, the olefin and paraffin in the mixture contain the same number of carbon atoms, e.g., propene/propane, butene/butane, pentene/pentane, isoprene/pentane, and hexene/hexane mixtures.

A commonly reported indicator of the efficacy of an olefin-paraffin separation is the separation or selectivity factor ($\alpha_{ij}$). The selectivity factor is commonly expressed by the following equation:

$$\alpha_{ij}=Q_i/Q_j \quad (10)$$

wherein $Q_i$ and $Q_j$ are the permeances of olefin and paraffin, respectively.

In general, the permeance of a component t can be found by using the following equation:

$$Q_t=y_t J/(P_f x_t - P_p y_t) \quad (11)$$

wherein $x_t$ and $Y_t$ are the mole fractions of component t in feed and permeate streams, respectively, J is the total permeate flux, typically in units of mL/s·cm$^2$, and $P_f$ and $P_p$ are pressures (e.g., cm of Hg) on the feed and permeate sides of the membrane, respectively.

The total permeate flux J provided by the ionic liquid is preferably at least $1.0 \times 10^{-4}$ mL/s·cm$^2$. In more preferred embodiments, J is at least $2.0 \times 10^{-4}$ mL/s cm$^2$, $3.0 \times 10^{-4}$ mL/s cm$^2$, $4.0 \times 10^{-4}$ mL/s·cm$^2$, $5.0 \times 10^{-4}$ mL/s·cm$^2$, $6.0 \times 10^{-4}$ mL/s cm$^2$, $7.0 \times 10^{-4}$ mL/s·cm$^2$, $8.0 \times 10^{-4}$ mL/s cm$^2$, $9.0 \times 10^{-4}$ mL/s·cm$^2$, $1.0 \times 10^{-3}$ mL/s cm$^2$, $2.0 \times 10^{-3}$ mL/s·cm$^2$, $3.0 \times 10^{-3}$ mL/s·cm$^2$, $4.0 \times 10^{-3}$ mL/s cm$^2$, $5.0 \times 10^{-3}$ mL/s·cm$^2$, or $6.0 \times 10^{-3}$ mL/s·cm$^2$, or a particular range between any two of the foregoing values. The selectivity factor ($\alpha_{ij}$) of the ionic liquid is preferably at least 5, and more preferably, at least 10, 20, 50, 100, 200, 300, 400, 500, 600, 700, 800, 900, or 1,000.

Examples have been set forth below for the purpose of illustration and to describe certain specific embodiments of the invention. However, the scope of this invention is not to be in any way limited by the examples set forth herein.

EXAMPLE 1

Preparation of Ag(DMBA)$_2$$^+$Beti$^-$ Ionic Liquid

N,N-dimethylbenzamide (DMBA) was first dissolved in water to obtain a DMBA aqueous solution, which was then added dropwise to an aqueous solution of $AgNO_3$. The mole ratio of DMBA to silver was about 2. A clear one-phase solution resulted, which was then converted to a biphasic system by mixing with an aqueous solution containing $Li^+Beti^-$ for anion exchange. The mole ratio of $Ag^+$ to $Beti^-$ was about 1.0. The lower (bottom) phase contained the hydrophobic ionic liquid $Ag(DMBA)_2^+Beti^-$. The ionic-liquid phase was washed with deionized (D.I.) water to ensure that all $LiNO_3$ residues were removed. Rotary evaporation was used to remove water and amide residues, thereby isolating the desired ionic liquid. The density was found by measuring the weight of three separate samples (1.0 mL each) at 25° C. and taking the mean of the three measurement values. The mean density possessed a relative standard uncertainty of less than 5%. The viscosity of the ionic liquid was measured using a viscometer (Grabner Instruments Minivis II). The ionic conductivity of the ionic liquid was measured with a conductivity meter (Corning CM II) at 25° C. The structure of $Ag(DMBA)_2^+Beti^-$ was confirmed using $^{13}C$ and $^1H$ NMR as follows. $^1H$-NMR data: δ, 7.11 (m, 5H), 2.73 (s, 3H), and 2.57 (s, 3H). $^{13}C$-NMR data: δ, 172.53 (CO), 135.98 (CH), 128.94 (CH), 127.52 (CH), 126.07 (CH), 118.02 ($CF_3$, qt, $J_{C-F}$=287.4 Hz, $J_{C-C-F}$=33.4 Hz), 111.72 ($CF_2$, tq, $J_{C-F}$=293.5 Hz, $J_{C-C-F}$=38.3 Hz), 38.78 ($CH_3$), and 34.91 ($CH_3$). Density at 23° C.: 1.49 g/mL. M.P.: −38.28° C. Viscosity at 23° C.: 184.5 cP. Conductivity at 23° C.: 0.652 mS/cm.

EXAMPLE 2

Preparation of $Ag(DBF)_2^+Beti^-$ Ionic Liquid

N,N-dibutylformamide (DBF) was added dropwise to an aqueous solution of $AgNO_3$. The mole ratio of DBF to silver was about 2. A clear one-phase solution resulted, which was then converted to a biphasic system by mixing with an aqueous solution containing $Li^+Beti^-$ for anion exchange. The mole ratio of $Ag^+$ to $Beti^-$ was about 1.0. The lower (bottom) phase contained the hydrophobic ionic liquid $[Ag(DBF)_2^+Beti^-]$. The ionic-liquid phase was washed with deionized (D.I.) water to ensure that all $LiNO_3$ residues were removed. Rotary evaporation was used to remove water and amide residues, thereby isolating the desired ionic liquid. Density, viscosity, and conductivity were measured as described in Example 1. The structure of $Ag(DBF)_2^+Beti^-$ was confirmed using $^{13}C$ and $^1H$ NMR as follows. $^1H$-NMR data: δ, 8.12 (s, 1H), 3.34 (m, 4H), 1.63 (m, 4H), 1.38 (m, 4H), and 0.97 (t, 6H, J=7.34 Hz). $^{13}C$-NMR data: δ, 164.89 (CHO), 118.17 ($CF_3$, qt, $J_{C-F}$=287.5 Hz, $J_{C-C-F}$=33.7 Hz), 111.84 ($CF_2$, tq, $J_{C-F}$=294.1 Hz, $J_{C-C-F}$=38.3 Hz), 47.84 ($CH_2$), 42.23 ($CH_2$), 30.46 ($CH_2$), 29.14 ($CH_2$), 19.89 ($CH_2$), 19.37 ($CH_2$), 13.21 ($CH_3$), and 13.02 ($CH_3$). Density at 23° C.: 1.22 g/mL. Viscosity at 23° C.: 97.65 cP. Conductivity at 23° C.: 0.445 mS/cm.

EXAMPLE 3

Preparation of $Ag(DEA)_2^+Beti^-$ Ionic Liquid

N,N-diethylacetamide (DEA) was added dropwise to an aqueous solution of $AgNO_3$. The mole ratio of DEA to silver was about 2. A clear one-phase solution resulted, which was then converted to a biphasic system by mixing with an aqueous solution containing $Li^+Beti^-$ for anion exchange. The mole ratio of $Ag^+$ to $Beti^-$ was about 1.0. The lower (bottom) phase contained the hydrophobic ionic liquid $[Ag(DEA)_2^+Beti^-]$. The ionic-liquid phase was washed with deionized (D.I.) water to ensure that all $LiNO_3$ residues were removed. Rotary evaporation was used to remove water and amide residues, thereby isolating the desired ionic liquid. Density was measured as described in Example 1. The structure of $Ag(DEA)_2^+Beti^-$ was confirmed using $^{13}C$ and $^1H$ NMR as follows. $^1H$-NMR data: δ, 3.34 (m, 4H), 2.08 (s, 3H), 1.15 (t, 3H, J=7.30 Hz) and 1.06 (t, 3H, J=7.22 Hz). $^{13}C$-NMR data: δ, 172.37 (CO), 117.87 ($CF_3$, qt, $J_{C-F}$=287.1 Hz, $J_{C-C-F}$=33.4 Hz), 111.65 ($CF_2$, tq, $J_{C-F}$=293.7 Hz, $J_{C-C-F}$=38.7 Hz), 43.40 ($CH_2$), 40.59 ($CH_2$), 20.50 ($CH_3$), 12.68 ($CH_3$), and 11.93 ($CH_3$). Density at 23° C.: 1.37 g/mL.

EXAMPLE 4

Preparation of $Ag(DIPF)_2^+Beti^-$ Ionic Liquid

N,N-diisopropylformamide (DIPF) was added dropwise to an aqueous solution of $AgNO_3$. The mole ratio of DIPF to silver was about 2. A clear one-phase solution resulted, which was then converted to a biphasic system by mixing with an aqueous solution containing $Li^+Beti^-$ for anion exchange. The mole ratio of $Ag^+$ to $Beti^+$ was about 1.0. The lower (bottom) phase contained the hydrophobic ionic liquid $[Ag(DIPF)_2^+Beti^+]$. The ionic-liquid phase was washed with deionized (D.I.) water to ensure that all $LiNO_3$ residues were removed. Rotary evaporation was used to remove water and amide residues, thereby isolating the desired ionic liquid. Density, viscosity, and conductivity were measured as described in Example 1. The structure of $Ag(DIPF)_2^+Beti^-$ was confirmed using $^{13}C$ and $^1H$ NMR as follows. $^1H$-NMR data: δ, 8.20 (s, 1H), 4.22 (m, 1H), 3.75 (m, 1H), and 1.30 (m, 12H). $^{13}C$-NMR data: δ, 164.13 (CHO), 117.99 ($CF_3$, qt, $J_{C-F}$=287.3 Hz, $J_{C-C-F}$=33.5 Hz), 111.81 ($CF_2$, tq, $J_{C-F}$=294.3 Hz, $J_{C-C-F}$=38.8 Hz), 45.59 (CH), 44.62 (CH), 22.20 ($CH_3$), and 19.17 ($CH_3$). Density at 23° C.: 1.36 g/mL. M.P.: −25.43° C. Viscosity at 23° C.: 114.0 cP. Conductivity at 23° C.: 0.745 mS/cm.

EXAMPLE 5

Preparation of $Ag(Olefin)^+Beti^-$ Ionic Liquid

In a typical synthesis, an olefin liquid (e.g., 1-pentene, 1-hexene, 1-octene, or isoprene) was added dropwise to an aqueous solution of $AgNO_3$, and the resulting cloudy solution was placed in an ice bath at 0° C. to prevent production of $AgO_x$. The mole ratio of olefin to silver was about 1.11. The cloudy solution subsequently became clear. After mixing with another solution containing $Li^+BETI^-$ to effect an anion exchange, a biphasic system resulted wherein the upper phase contained the ionic liquid. The mole ratio of $Ag^+$ to $BETI^-$ was about 1.0. The ionic liquid was separated and then washed with D.I. water to ensure removal of any remaining $LiNO_3$ residue. Rotary evaporation was used to remove water and olefin residues, thereby isolating the desired ionic liquid. Density and conductivity were measured as described in Example 1. The structure of $Ag(1-hexene)^+Beti^-$ was confirmed using $^{13}C$ and $^1H$ NMR as follows. $^1H$-NMR data: δ, 6.50 (m, 1H), 5.28 (m, 2H), 2.24 (m, 2H), 1.42 (m, 4H) and 0.94 (t, 3H, J=7.22 Hz). $^{13}C$-NMR data: δ, 139.83 (CH), 117.52 ($CF_3$, qt, $J_{C-F}$=288.1 Hz, $J_{C-C-F}$=33.3 Hz), 111.91 ($CF_2$, tq, $J_{C-F}$=294.1 Hz, $J_{C-C-F}$=38.7 Hz), 33.81 ($CH_2$), 102.34 ($CH_2$), 31.59 ($CH_2$), 22.01 ($CH_2$), and 13.55 ($CH_3$). Density at 23° C.: 1.61 g/mL. The structure of $Ag(1-octene)^+Beti^-$ was confirmed using $^{13}C$ and $^1H$ NMR as follows. $^1H$-NMR data: δ, 6.51 (m, 1H), 5.26 (m, 2H), 2.34 (m, 2H), 1.47 (m, 2H), 1.29 (m, 6H) and 0.88 (t, 3H, J=7.22 Hz). $^{13}C$-NMR data: δ, 140.27 (CH), 117.58 ($CF_3$, qt, $J_{C-F}$=288.2

Hz, $J_{C\text{-}C\text{-}F}$=33.5 Hz), 111.98 (CF$_2$, tq, $J_{C\text{-}F}$=297.1 Hz, $J_{C\text{-}C\text{-}F}$=39.7 Hz), 103.27 (CH$_2$), 34.07 (CH$_2$), 31.37 (CH$_2$), 29.39 (CH$_2$), 28.56 (CH$_2$), 22.41 (CH$_2$), and 13.84 (CH$_3$). Density at 23° C.: 1.46 g/mL. Conductivity at 23° C.: 0.473 mS/cm.

EXAMPLE 6

Preparation of Ag(CH$_3$CN)$_2$$^+$Beti$^-$ Ionic Liquid

Acetonitrile was added dropwise to an aqueous solution of AgNO$_3$. The mole ratio of DIPF to silver was about 2. A clear one-phase solution resulted, which was then converted to a biphasic system by mixing with an aqueous solution containing Li$^+$Beti$^-$ for anion exchange. The mole ratio of Ag$^+$ to Beti$^-$ was about 1.0. The lower (bottom) phase contained the hydrophobic ionic liquid [Ag(CH$_3$CN)$_2$$^+$Beti$^-$]. The ionic-liquid phase was washed with deionized (D.I.) water to ensure that all LiNO$_3$ residues were removed. Rotary evaporation was used to remove water and amide residues, thereby isolating the desired ionic liquid. Density, viscosity, and conductivity were measured as described in Example 1. The structure of Ag(CH$_3$CN)$_2$$^+$Beti$^-$ was confirmed using $^{13}$C and $^1$H NMR as follows. $^1$H-NMR data: δ, 2.04 (s, 3H). $^{13}$C-NMR data: δ, 119.52 (CN), 117.68 (CF$_3$, qt, $J_{C\text{-}F}$=286.9 Hz, $J_{C\text{-}C\text{-}F}$=33.3 Hz), 111.58 (CF$_2$, tq, $J_{C\text{-}F}$=294.1 Hz, $J_{C\text{-}C\text{-}F}$=38.7 Hz), and 0.35 (CH$_3$). Density at 23° C.: 1.81 g/mL. M.P.: −75.82° C. Viscosity at 23° C.: 84.97 cP. Conductivity at 23° C.: 2.335 mS/cm.

While there have been shown and described what are at present considered the preferred embodiments of the invention, those skilled in the art may make various changes and modifications which remain within the scope of the invention defined by the appended claims.

What is claimed is:

1. An ionic liquid comprising (i) a cationic portion containing a complex of a silver (I) ion and one or more neutral ligands selected from the group consisting of organoamines and olefins, and (ii) an anionic portion having the chemical formula:

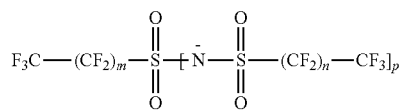

(5)

wherein m and n are independently 0 or an integer of 1 or above, and p is 0 or 1, provided that when p is 0, the group —N—SO$_2$—(CF$_2$)$_n$CF$_3$ subtended by p is replaced with an oxide atom connected to the sulfur atom, and when p is 1, the shown perfluoroalkyl groups can optionally crosslink to form a cyclic anion;
further provided that said organoamines exclude saturated primary amines containing up to four carbon atoms, and said olefins exclude olefins containing up to six carbon atoms, and when the neutral ligand is a saturated primary amine or an olefin, then m and n are not both 0.

2. The ionic liquid of claim 1, wherein the one or more neutral ligands are selected from organoamines.

3. The ionic liquid of claim 2, wherein said organoamines are primary amines.

4. The ionic liquid of claim 1, wherein the one or more neutral ligands are selected from olefins.

5. The ionic liquid of claim 4, wherein said olefins contain up to eighteen carbon atoms.

6. The ionic liquid of claim 1, wherein said anionic portion has the chemical formula:

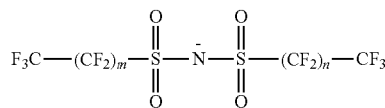

(6)

wherein m and n are independently 0 or an integer of 1 or above.

7. The ionic liquid of claim 6, wherein m and n are independently a number from 0 to 11.

8. The ionic liquid of claim 6, wherein m and n are both at least 1.

9. The ionic liquid of claim 1, wherein said anionic portion has the chemical formula:

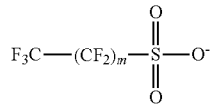

(8)

wherein m is 0 or an integer of at least 1.

10. The ionic liquid of claim 9, wherein m is a number from 0 to 11.

11. An olefin-paraffin separation membrane comprising a layer of the ionic liquid of claim 1 on an inert gas-permeable support.

12. The olefin-paraffin membrane of claim 11, wherein said inert gas-permeable support comprises an alumina support.

13. A method for separating an olefin from a paraffin contained in a gaseous olefin-paraffin mixture, the method comprising passing said gaseous olefin-paraffin mixture through a layer of the ionic liquid of claim 1.

14. The method of claim 13, wherein the olefin in said gaseous olefin-paraffin mixture contains up to six carbon atoms, and the paraffin is a straight-chained, branched, or cyclic alkane containing up to six carbon atoms.

15. The method of claim 14, wherein the olefin in said gaseous olefin-paraffin mixture contains at least three and up to six carbon atoms, and the paraffin is a straight-chained, branched, or cyclic alkane containing up to six carbon atoms.

16. An ionic liquid comprising (i) a cationic portion containing a complex of a silver (I) ion and one or more organonitrile neutral ligands, and (ii) an anionic portion having the chemical formula:

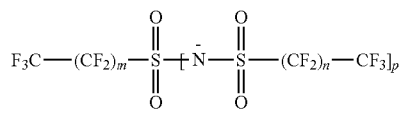

(5)

wherein m and n are independently 0 or an integer of 1 or above, and p is 0 or 1, provided that when p is 0, the group —N—SO$_2$—(CF$_2$)$_n$CF$_3$ subtended by p is replaced with an oxide atom connected to the sulfur atom, and when p is 1, the shown perfluoroalkyl groups can optionally crosslink to form a cyclic anion.

17. The ionic liquid of claim 16, wherein the organonitriles have the following chemical formula:

$$R_8-(CN)_t \qquad (4)$$

wherein subscript t is 1 or 2 to indicate the presence of 1 or 2 cyanide groups, respectively, and $R_8$ is a hydrocarbon group containing at least one and up to eight carbon atoms when t is 1, or a hydrocarbon linker containing at least one and up to eight carbon atoms when t is 2.

18. The ionic liquid of claim 17, wherein $R_8$ is an alkyl group containing at least one and up to eight carbon atoms when t is 1, or an alkyl linker containing at least one and up to eight carbon atoms when t is 2.

19. The ionic liquid of claim 18, wherein the organonitriles are selected from the group consisting of acetonitrile, propionitrile, butyronitrile, valeronitrile, capronitrile, heptanenitrile, octanenitrile, malononitrile, succinonitrile, glutaronitrile, adiponitrile, pimelonitrile, suberonitrile, azelanitrile, and sebaconitrile.

* * * * *